US012616487B2

(12) United States Patent
Stone

(10) Patent No.: US 12,616,487 B2
(45) Date of Patent: May 5, 2026

(54) MINIMALLY INVASIVE SURGERY LAPIDUS SYSTEM

(71) Applicant: Acumed LLC, Hillsboro, OR (US)

(72) Inventor: Nathan Stone, Addison, TX (US)

(73) Assignee: Acumed LLC, Hillsboro, OR (US)

( * ) Notice: Subject to any disclaimer, the term of this patent is extended or adjusted under 35 U.S.C. 154(b) by 0 days.

(21) Appl. No.: 18/428,138

(22) Filed: Jan. 31, 2024

(65) Prior Publication Data

US 2024/0252186 A1 Aug. 1, 2024

Related U.S. Application Data

(60) Provisional application No. 63/442,672, filed on Feb. 1, 2023.

(51) Int. Cl.
| | |
|---|---|
| *A61B 17/17* | (2006.01) |
| *A61B 17/15* | (2006.01) |
| *A61B 17/88* | (2006.01) |
| *A61B 17/56* | (2006.01) |

(52) U.S. Cl.
CPC ........ *A61B 17/1775* (2016.11); *A61B 17/151* (2013.01); *A61B 17/171* (2013.01); *A61B 17/1725* (2013.01); *A61B 17/8866* (2013.01); *A61B 2017/565* (2013.01)

(58) Field of Classification Search
CPC . A61B 17/151; A61B 17/8866; A61B 17/171; A61B 7/1725; A61B 17/775
See application file for complete search history.

(56) References Cited

U.S. PATENT DOCUMENTS

| | | | |
|---|---|---|---|
| 2012/0136359 A1 | 5/2012 | Grunder et al. | |
| 2016/0235414 A1 | 8/2016 | Hatch et al. | |
| 2018/0177509 A1 | 6/2018 | Trabish et al. | |
| 2018/0185079 A1 | 7/2018 | Smith et al. | |
| 2019/0183514 A1 | 6/2019 | Sah | |
| 2022/0370211 A1* | 11/2022 | Campbell | A61B 17/151 |
| 2023/0190352 A1* | 6/2023 | Coyne | A61B 17/8095 |
| | | | 606/87 |
| 2023/0240720 A1* | 8/2023 | Schmidt | A61B 17/151 |
| | | | 623/53 |
| 2023/0263542 A1* | 8/2023 | Denham | A61B 17/151 |
| | | | 606/87 |

(Continued)

FOREIGN PATENT DOCUMENTS

WO 2023044085 A1 3/2023

OTHER PUBLICATIONS

International Search Report corresponding to related International Application No. PCT/US2024/013799 date of mailing Jun. 17, 2024, 3 pages.

(Continued)

*Primary Examiner* — Matthew J Lawson
(74) *Attorney, Agent, or Firm* — Knobbe, Martens, Olson & Bear, LLP

(57) ABSTRACT

A system includes a cutting guide having a base body configured to be fixed to a first bone of a patient and a cutting slot block configured to provide a guide for cutting at least one of the first bone and a second bone of the patient. The cutting slot block is rotationally coupled to the base body. The cutting slot block is configured to rotate in a first rotational direction. The cutting guide comprises a distal portion and a proximal portion.

32 Claims, 15 Drawing Sheets

(56)  References Cited

U.S. PATENT DOCUMENTS

2024/0032955 A1* 2/2024 Schmidt ................. A61B 17/28
2024/0252219 A1* 8/2024 Pepin ................. A61B 17/8866

OTHER PUBLICATIONS

International Written Opinion corresponding to related International Application No. PCT/US2024/013799 date of mailing Jun. 17, 2024, 7 pages.

* cited by examiner

MINIMALLY INVASIVE SURGERY LAPIDUS SYSTEM

PRIORITY CLAIM

This application claims priority to U.S. Provisional Patent Application No. 63/442,672 filed on Feb. 1, 2023, the entire contents of which are hereby incorporated by reference and relied upon.

BACKGROUND

Lapidus procedure refers to a surgical procedure for the treatment of a bunion deformity. A bunion is a bony bump that is formed on the side of the big toe joint, which may cause a foot deformity. Lapidus procedure involves the correction of the foot structure by repositioning the poorly aligned first metatarsal bone to its proper position.

Lapidus procedures traditionally require full exposure of the first metatarsophalangeal (TMT) joint. This means that traditionally an incision having a length of at least 3.5 cm is needed to complete the Lapidus procedure, which may leave a big scar, require more healing time, and have a risk of infection.

SUMMARY

The present disclosure provides new and innovative systems and methods for minimally invasive Lapidus surgery. In some examples, a system according to the present disclosure may include a cutting guide having a base body configured to be fixed to a first bone of a patient and a cutting slot block configured to provide a guide for cutting at least one of the first bone and a second bone of the patient. The cutting slot block may be rotationally coupled to the base body. The cutting slot block may be configured to rotate in a first rotational direction.

In some examples, a method according to the present disclosure may include fixing the base body of the cutting guide to the first bone of the patient, positioning the cutting slot block in a first angle, cutting one of the first bone and the second bone by inserting, through a slot of the cutting slot block in the first angle, a bone cutting device into an incision between the first bone and the second bone, rotating the cutting slot block to a second angle different from the first angle, and cutting one of the first bone and the second bone by inserting, through the slot of the cutting slot block in the second angle, the bone cutting device into the incision.

Additional features and advantages of the disclosed systems are described in, and will be apparent from, the following Detailed Description and the Figures.

DETAILED DESCRIPTION OF EXAMPLE EMBODIMENTS

The present disclosure is directed to systems and methods for minimally invasive Lapidus surgery. As discussed above, the conventional Lapidus procedure may require an incision having a length of at least 3.5 cm, which may have various issues such as a big scar, more healing time, and infection risk. Moreover, conventional devices for the Lapidus procedure may only allow a single (sagittal) plane correction, requiring the surgeon to perform the correction in other planes (e.g., frontal and transverse planes) manually, which may necessitate a bigger incision size, and reduce the accuracy and repeatability of the procedure.

Aspects of the present disclosure may address the above-discussed issue in the conventional Lapidus procedure. For example, aspects of the present disclosure may provide a system having a cutting guide, a first reposition guide, and/or a second reposition guide, which allows a multi-planar (sagittal, frontal, and transverse planes) correction of the bone (e.g., first metatarsal bone). Moreover, since multiple planes can be corrected using the system according to the present disclosure, the accuracy and repeatability of the Lapidus procedure can be improved.

Moreover, the cutting guide according to the present disclosure may allow the surgeon to make two (un-parallel) cuts that may have almost the same starting point, which may enable the Lapidus surgery to be performed with a smaller incision (e.g., around 3 mm) than the traditional approaches (e.g., having an approximately 3 cm incision). This may reduce the size of the scar, healing times, and risk of infection compared to the traditional full exposure techniques.

Figure 1:
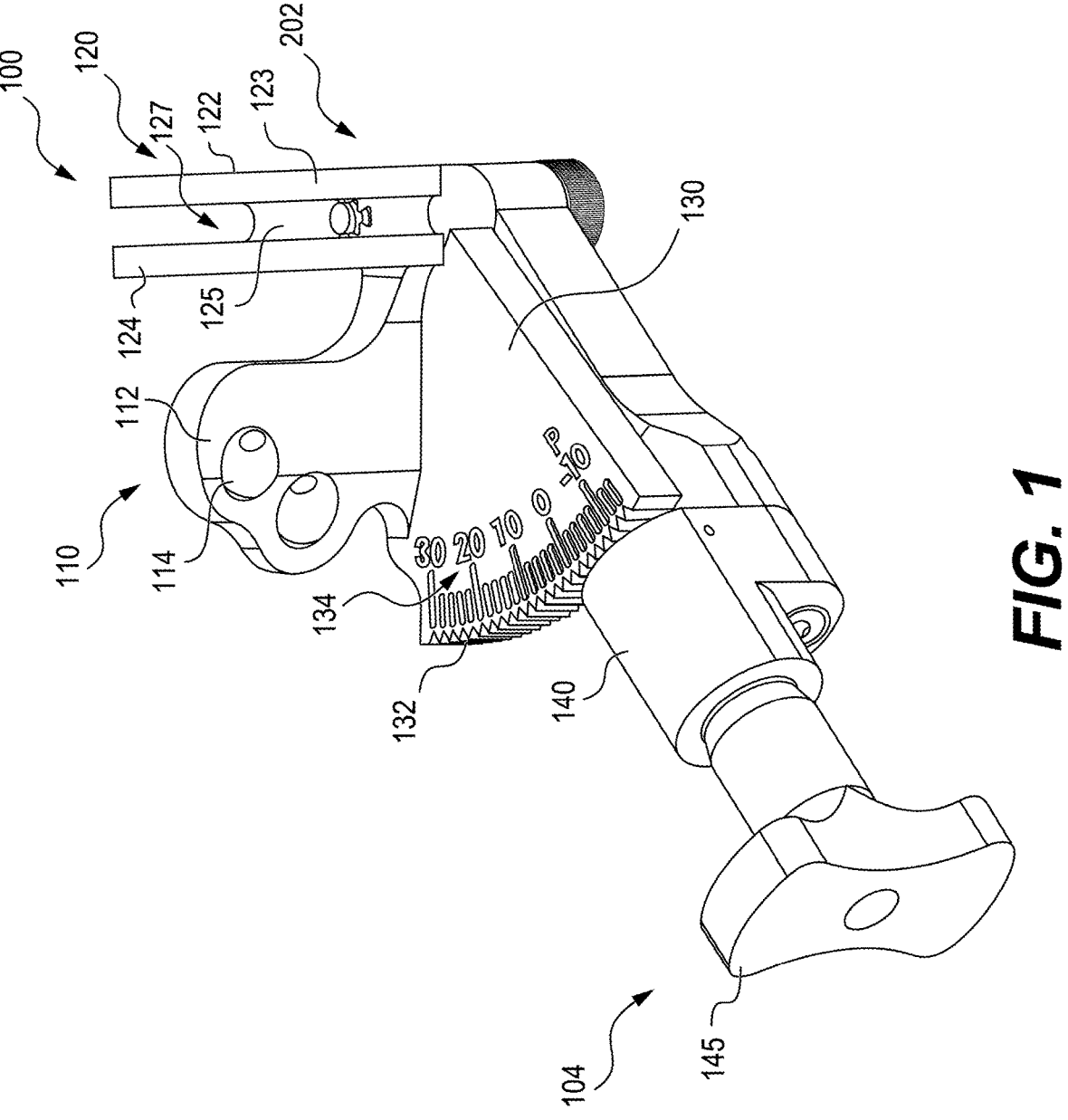
FIG. 1 is a diagram of a perspective view of a cutting guide according to an example embodiment of the present disclosure.
Figure 2:
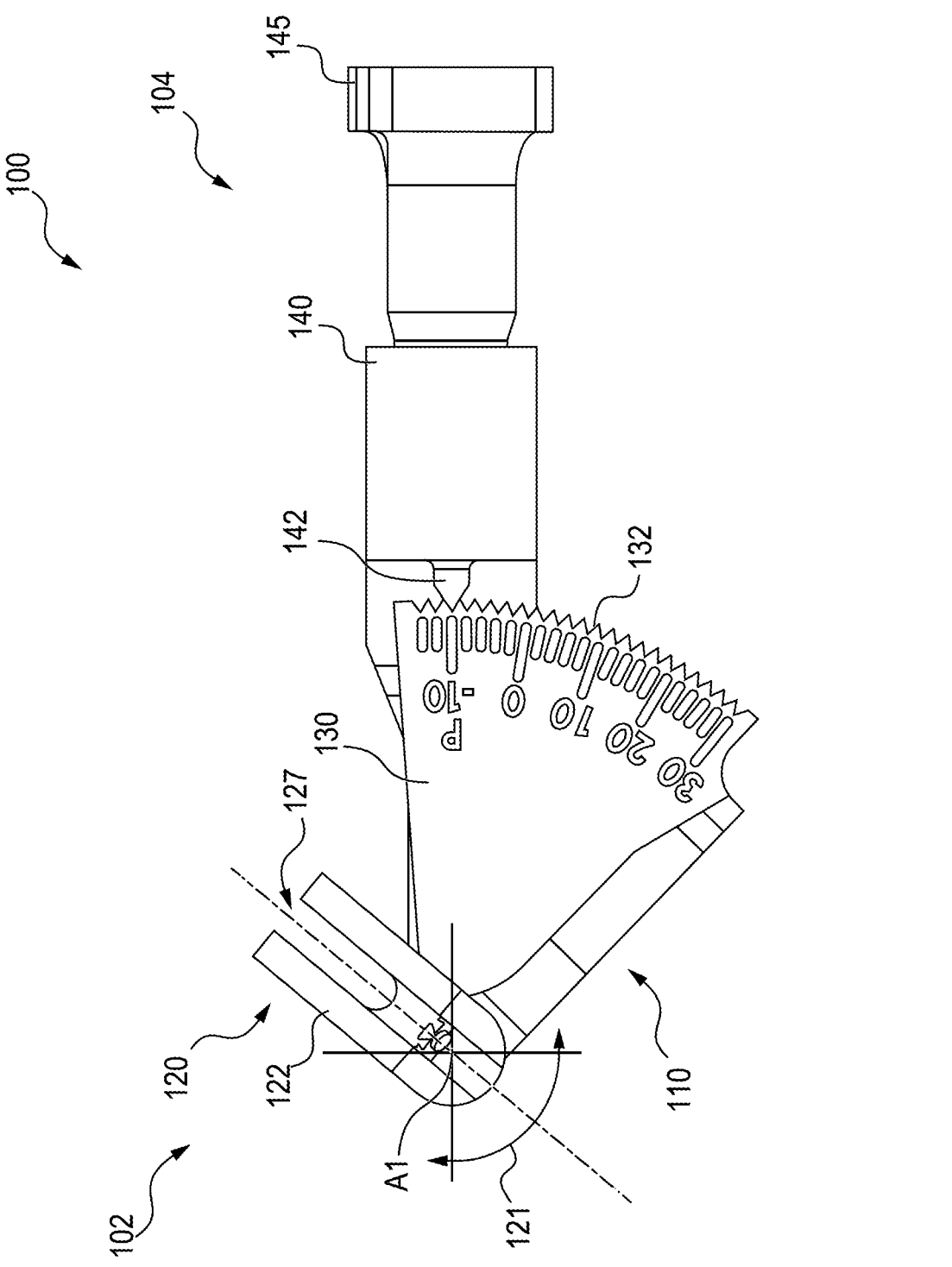
FIG. 2 is a diagram of a top view of the cutting guide of FIG. 1.

FIGS. 1 and 2 depict an example cutting guide 100 according to an example of the present disclosure. The cutting guide 100 may have a distal portion 102 and a proximal portion 104. The cutting guide 100 may include a base body 110 and a cutting slot block 120, for example, at or near the distal portion 102.

In some examples, the base body 110 may be fixed to a bone of a patient (e.g., medial cuneiform bone). In some examples, the base body 110 may include a first fixing block 112. The first fixing block 112 may include a first fixing mechanism 114 for fixing the base body 110 (including the first fixing block 112) to a bone of the patient. In some examples, the first fixing mechanism may be one or more holes 114 formed on the first fixing block 112. The one or more holes 114 may be configured to receive a bone fastener. In some examples, the bone fastener may be a pin, a screw, a tack, or a k-wire. In other examples, the bone fastener may be any other suitable fastening device that can (temporally or removably) fix the base body 110/first fixing block 112 to the bone of a patient. In some examples, the bone fastener may include a hat that may prevent the bone fastener from penetrating into the bone deeper than a predetermined length (so that it does not penetrate into another bone unintentionally). In some examples, the first fixing mechanism may be a clamp or any other suitable device that can (temporally or removably) fix the base body 110/first fixing block 112 to the bone of a patient (e.g., medial cuneiform bone).

The cutting slot block 120 may be configured to provide a guide for cutting one or more bones of the patient (e.g., medial cuneiform bone, first metatarsal bone). The cutting slot block 120 may be rotationally coupled to the base body 110/first fixing block 112. The cutting slot block 120 may include a rotation axis A1. The cutting slot block 120 may rotate in a first rotational direction 121, for example, around the rotation axis A1. In some examples, the first rotational direction 121 may be in a first plane. The first plane may be a transverse plane or substantially parallel to the transverse plane (for example, when the cutting guide 100 is attached to the human body).

In some examples, the difference between a maximum angle and a minimum angle of the cutting slot block 120 may be at least 15°, at least 20°, at least 25°, at least 30°, or in a range of about 15° to about 40°, for example, about 15° to about 25°, about 25° to about 35°, and/or about 35° to about 40°. In other examples, the difference between a maximum angle and a minimum angle of the angular marking 134 may have any other suitable value (e.g., lower than 15° or greater than 40°).

The cutting slot block 120 may include a cutting slot guide body 122 and a slot 127 defined by the cutting slot guide body 122. In some examples, the slot 127 may be formed in or on the cutting slot guide body 122. The slot 127 (in combination with the cutting slot guide body 122) may provide a guide for a bone cutting device. Examples of the bone cutting device may include a bur, a blade, an osteotome, and a reciprocating saw. In some examples, the cutting slot guide body 122 may include a first plate 123 and a second plate 124. A bottom portion of the first plate 123 and the second plate 124 may be connected to each other through a connecting portion 125. The slot 127 may be defined by the first plate 123, second plate 124, and connecting portion 125. In other examples, the cutting slot block 120/cutting slot guide body 122/slot 127 may have any other suitable shape/structure (e.g., one or more bars/rods/plates with or without one or more holes/slots/grooves) as long as it can guide a bone cutting device.

In some examples, the cutting guide 100 may include a gauge block 130. The gauge block 130 may be configured to provide an indication of an angle of the cutting slot block 120. The gauge block 130 may be used to measure the angle of the cutting slot block 120. For example, the gauge block 130 may have an angular marking 134 (e.g., from −10° to 30°). The angular marking 134 may be disposed on an upper surface and/or a side surface of the gauge block 130.

In FIGS. 1 and 2, the maximum angle and minimum angle in the angular marking 134 are shown as 30° and −10°, respectively, and the difference between these two angles is 40°. However, the angular marking 134 may have any other suitable angle values. In some examples, the difference between a maximum angle and a minimum angle of the angular marking 134 may be at least 15°, at least 20°, at least 25°, at least 30°, or in a range of about 15° to about 40°, for example, about 15° to about 25°, about 25° to about 35°, and/or about 35° to about 40°. In other examples, the difference between a maximum angle and a minimum angle of the angular marking 134 may have any other suitable value (e.g., lower than 15° or greater than 40°).

In some examples, the cutting guide 100 may further include a rotation arm 140. The rotation arm 140 may extend outward from the distal portion 102 (e.g., rotation axis A1 of the cutting slot block 120), for example, to the proximal portion 104 of the cutting guide 110. The rotation arm 140 may rotate relative to the base body 110/first fixing block 112/gauge block 130. The rotation arm 140 may rotate in the first rotational direction 121 around the rotation axis A1. In some examples, the cutting slot block 120, the gauge block 130, and the rotation arm 140 may be coupled to the same hinge point/pin and rotate around the hinge point/pin, which may serve as a rotation axis (e.g., rotation axis A1).

In some examples, the rotation arm 140 may be coupled to the cutting slot block 120. The rotation arm 140 may rotate the cutting slot block 120 relative to the base body 110/first fixing block 112. That is, the rotation of the rotation arm 140 may cause the rotation of the cutting slot block 120. In other examples, the rotation of the rotation arm 140 may be independent of the rotation of the cutting slot block 120.

In some examples, the rotation arm 140 may include a first engagement structure 142. The first engagement structure 142 may be configured to engage and disengage the rotation arm 140 with and from the base body 110/gauge block 130. The base body 110/gauge block 130 may include a second engagement structure 132. The second engagement structure 132 may be configured to be engaged with the first engagement structure 142. In some examples, the first engagement structure 142 may be a (spring-loaded) blade and the second engagement structure may be a plurality of notches. In other examples, the first and second engagement structures 142, 132 may have any other suitable structures that can be engaged/disengaged with/from each other (e.g., worm gear/threaded component—notches).

In some examples, the rotation arm 140 may further include a graspable device (e.g., knob) 145 coupled to the first engagement structure 142. The first engagement structure 142 may be engaged/disengaged with/from the second engagement structure 132 via the graspable device 145. For example, when the graspable device 145 is pulled in one direction (e.g., toward the proximal portion 104 of the cutting guide 100), the first engagement structure 142 may be disengaged from the second engagement structure 142. When the graspable device 145 is pushed in a second direction (e.g., toward the distal portion 102 of the cutting guide 100) opposite the first direction, the first engagement structure 142 may be engaged with the second engagement structure 142. In some examples, the first engagement structure 142 may be spring-loaded, and the graspable device 145 may be pushed in the second direction automatically when the force that has pulled the graspable device 145 in the first direction is removed.

In some examples, the first engagement structure 142 may serve as an indicator that may point to the angular marking 134. For example, as shown in FIG. 2, the first engagement structure 142 (e.g., blade) may indicate the angle of the rotation arm 140/cutting slot block 120 (e.g., −10° in FIG. 2) relative to the angular marking 134. In some examples, an indicator may be provided on the cutting slot block 120, the base body 110, or the rotation arm 140.

In some examples, the rotation arm 140 may include a locking mechanism. For example, if the graspable device 145 may be turned a predetermined degree (e.g., 45° or 90°) in one direction (e.g., counterclockwise) while the first engagement structure 142 is engaged with the second engagement structure 132, the rotation arm 140 may be locked with the base body 110/gauge block 130 and the graspable device 145 cannot be pulled in the first direction. In order to unlock the rotation arm 140, the graspable device 145 may be turned a predetermined degree (e.g., 45° or 90°) in another direction (e.g., clockwise). In this way, the locking mechanism can lock the angle of the rotation arm 140 relative to the base body 110/gauge block 130. When the rotation arm 140 rotates with the cutting slot block 120, the locking mechanism of the rotation arm 140 can also lock the angle of the cutting slot block 120 relative to the base body 110/gauge block 130.

In some examples, the gauge block 130 may be part of the base body 110. In this case, the gauge block 130 may be integral and/or permanently fixed with the first fixing block 112 as shown in FIGS. 1 and 2.

In other examples, the gauge block 130 may be separate from the base body 110/first fixing block 112. In some examples, the gauge block 130 may be coupled to/moved with the cutting slot block 120. In this case, the rotation arm 140 may rotate independently of the cutting slot block 120.

Figure 3:
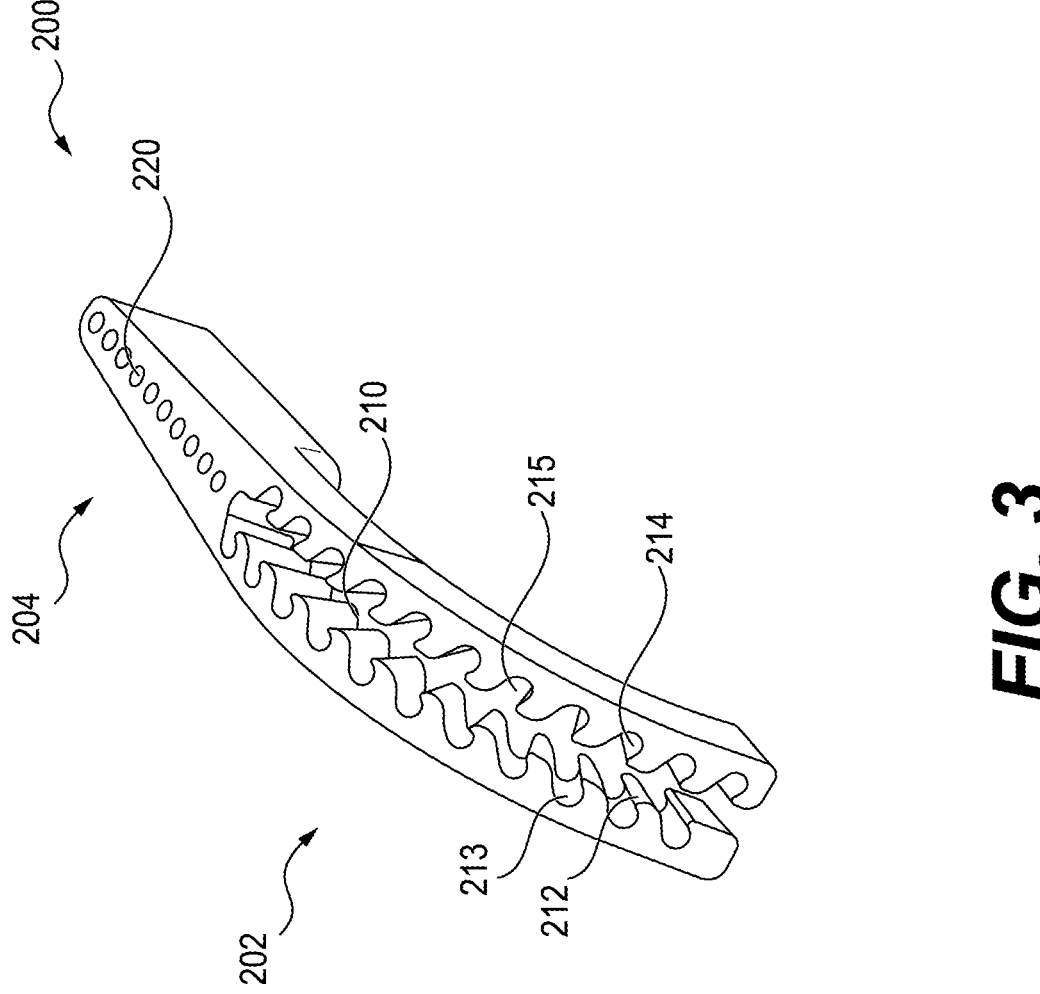
FIG. 3 is a diagram of a perspective view of a first reposition guide block according to an example embodiment of the present disclosure.
Figures 4, 5:
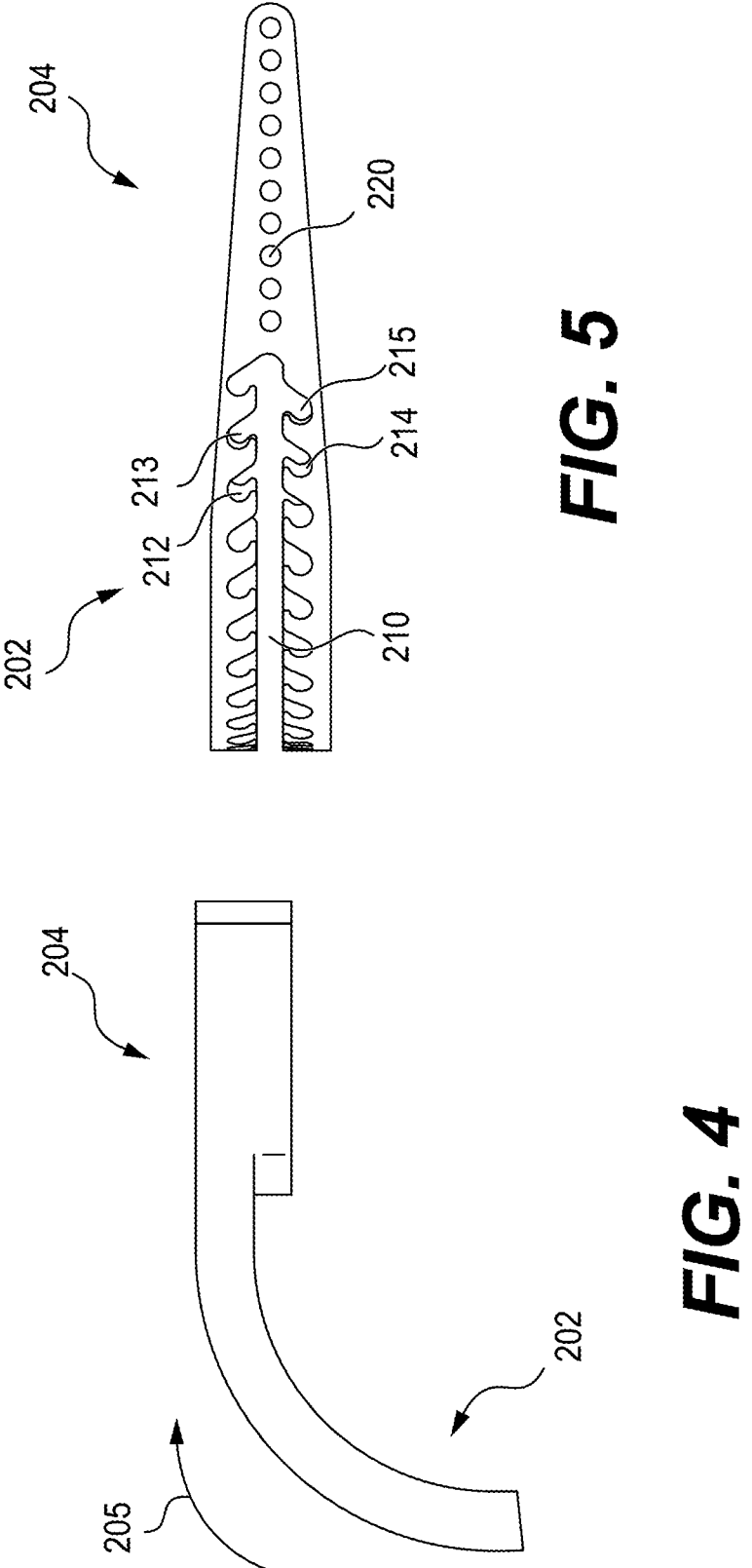
FIG. 4 is a diagram of a side view of the first reposition guide block of FIG. 3.
FIG. 5 is a diagram of a top view of the first reposition guide block of FIG. 3.

FIGS. 3 to 5 illustrate a first reposition guide block 200 according to an example embodiment of the present disclosure. In some examples, the system according to the present disclosure may further include a first reposition guide block 200. The first reposition guide block 200 may provide a guide for rotating the bone of the patient (e.g., first metatarsal bone), for example, in a second rotational direction 205. The second rotational direction 205 may be in a second plane. The second plane may be a frontal plane or substantially parallel to the frontal plane (for example, when the first reposition guide block 200 is attached to the human body).

The first reposition guide block 200 may include a first portion 202 and a second portion 204. In some examples, the first portion 202 may be curved. In other examples, the first portion 202 may have any other suitable shape (e.g., straight bar with or without one or more bent points).

The first portion 202 may include an elongated slot 210. The elongated slot 210 may be provided to receive a bone fastener. The bone fastener may be inserted into the elongated slot 210 (and ultimately into the bone of the patient percutaneously) and can be moved along the elongated slot 210 in the second rotational direction 205. The elongated slot 210 may include a first elongated surface 212 and a second elongated surface 214 opposite the first elongated surface 212. The first elongated surface 212 and/or the second elongated surface 214 may include a plurality of grooves 213/215 configured to receive the bone fastener. The grooves 213/215 may be sized to securely receive the bone fastener or may be sized smaller than the bone fastener. In this way, the bone of the patient (e.g., first metatarsal bone) can be rotated for the second (frontal) plane correction and/or temporarily fixed at a desired position during surgery.

In some examples, the second portion 204 of the first reposition guide block 200 may include one or more holes 220. The one or more holes 220 may be provided to receive a bone fastener. For example, the bone fastener may be inserted into the one or more holes 220 of the second portion 204 and ultimately into the one or more bones of the patient (e.g., second and/or third metatarsal bone), for example, percutaneously. In this way, the first reposition guide block 200 can be stably fixed with the body/bones (other than the bone, such as the first metatarsal bone, that is supposed to be corrected/rotated) of the patient.

Figure 6:
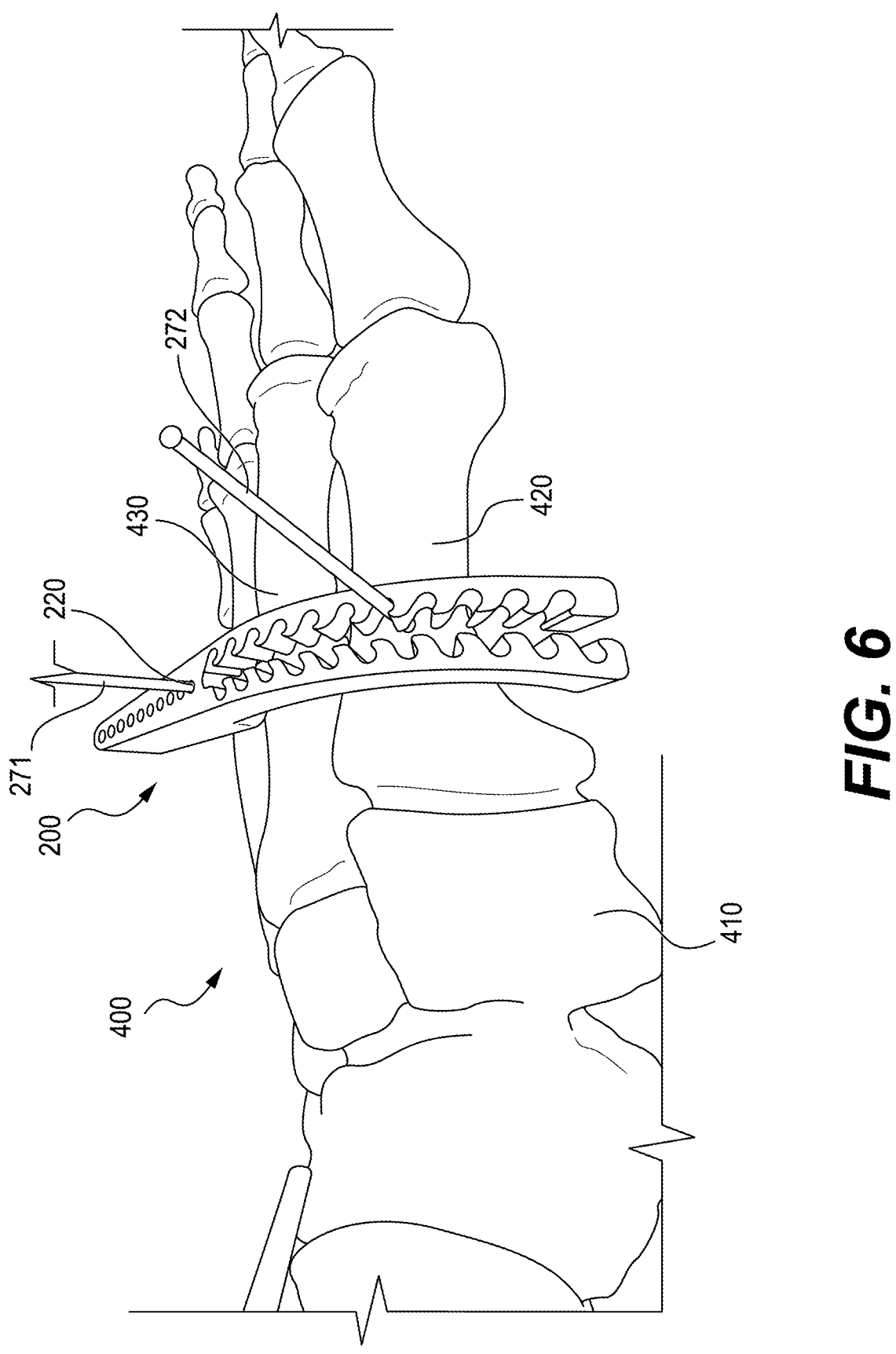
FIG. 6 is a diagram of the first reposition guide block of FIG. 3 applied to human bones.

FIG. 6 illustrates the first reposition guide block 200 of FIG. 3 applied to human bones. In FIG. 6, the skin of the foot is omitted for illustrative purposes only. As shown in FIG. 6, a first bone fastener 271 may pass a hole 220 in the second portion 204 of the first reposition guide block 200 and be inserted into the second metatarsal bone 430, for example, to temporarily fix the first reposition guide block 200 with the body (e.g., foot) of the patient. A second bone fastener 272 may pass the elongated slot 210 and be inserted into the first metatarsal bone 420 located next to the medial cuneiform bone 410. A side portion of the second bone fastener 272 may be inserted into or placed around a groove 213/215 formed on a (first/second) elongated surface, for example, to temporarily fix the second bone fastener 272 (and ultimately the first metatarsal bone) at a desired position during surgery.

Figure 7:
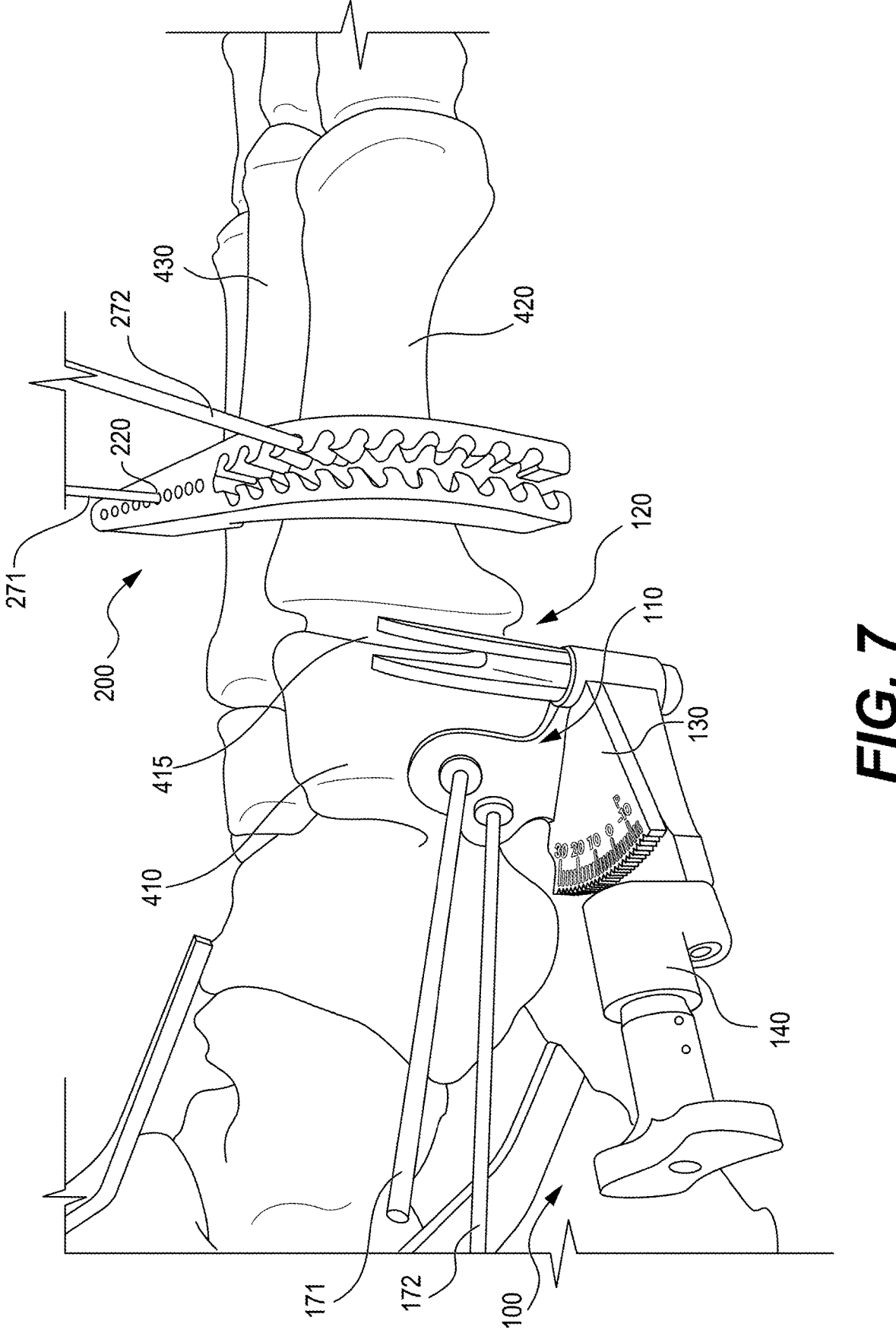
FIG. 7 is a diagram of both of the cutting guide of FIG. 1 and the first reposition guide block of FIG. 3 applied to human bones.

FIG. 7 illustrates the cutting guide 100 of FIG. 1 and the first reposition guide block 200 of FIG. 3 applied to human bones. As shown in FIG. 7, a first bone fastener 171 and a second bone fastener 172 may pass the holes 114 formed on/in the base body 110/first fixing block 112 and be inserted into the medial cuneiform bone 410, for example, to temporarily fix the base body 110/first fixing block 112 with the body (e.g., foot) of the patient. At this time, the cutting slot block 120 may be positioned adjacent the joint between the medial cuneiform bone 410 and the first metatarsal bone 420. The first and second bone fasteners 171/172 may be positioned such that they do not intersect one another or the joint.

Figure 8:
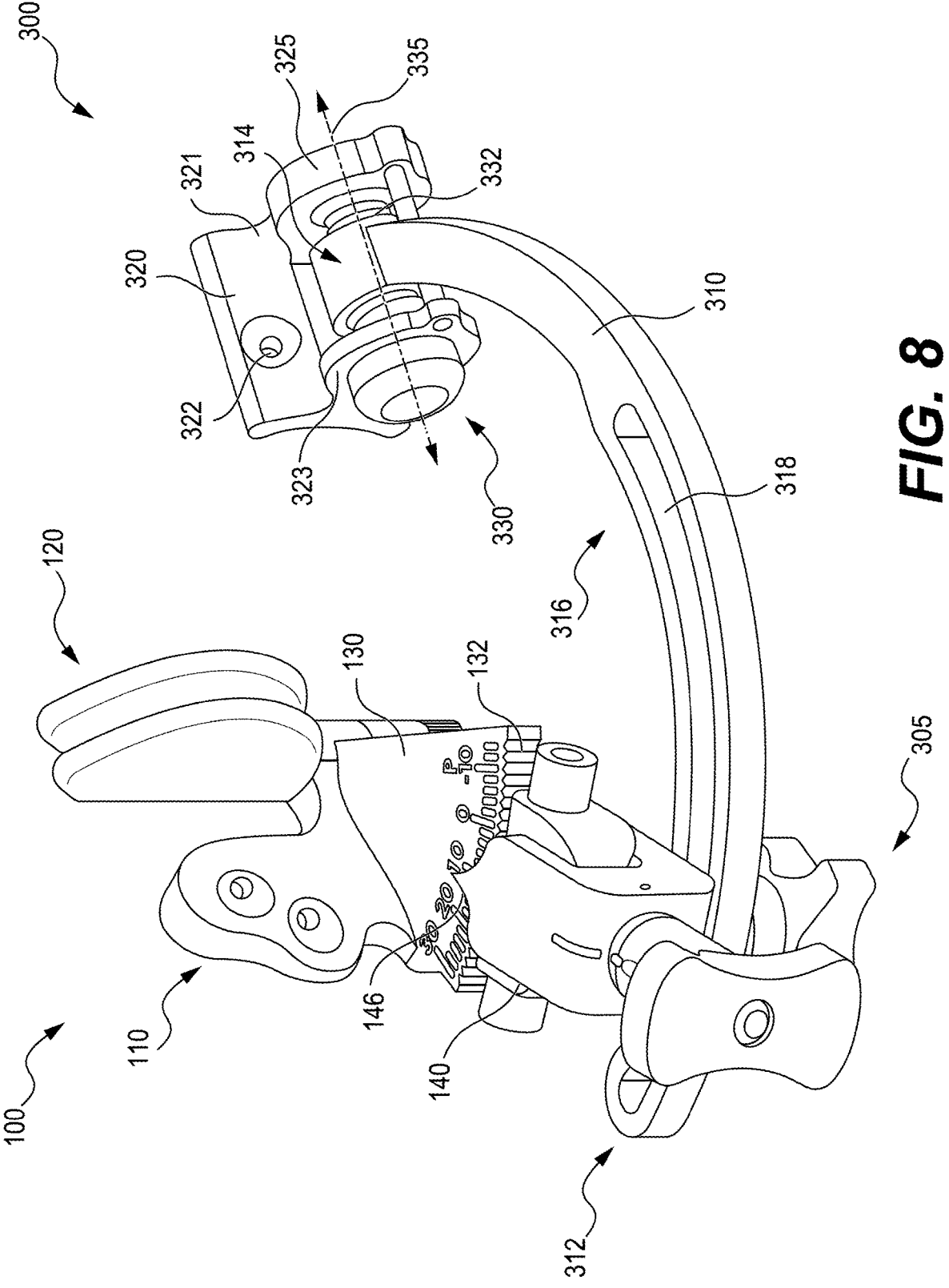
FIG. 8 is a diagram of a perspective view of a second reposition guide block applied to a cutting guide according to an example embodiment of the present disclosure.
Figure 9:
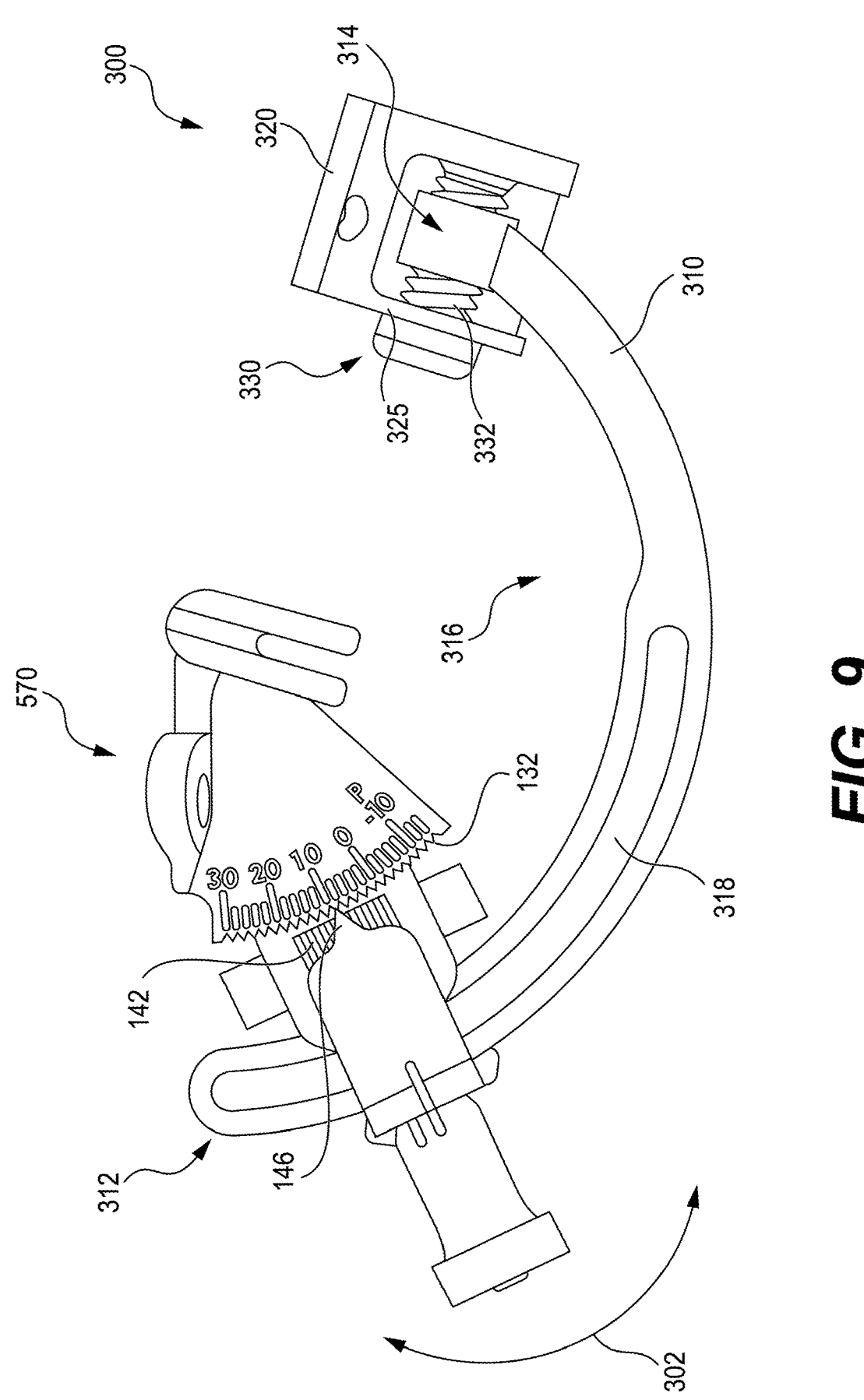
FIG. 9 is a diagram of a top view of the second reposition guide block and cutting guide of FIG. 8.
Figure 10:
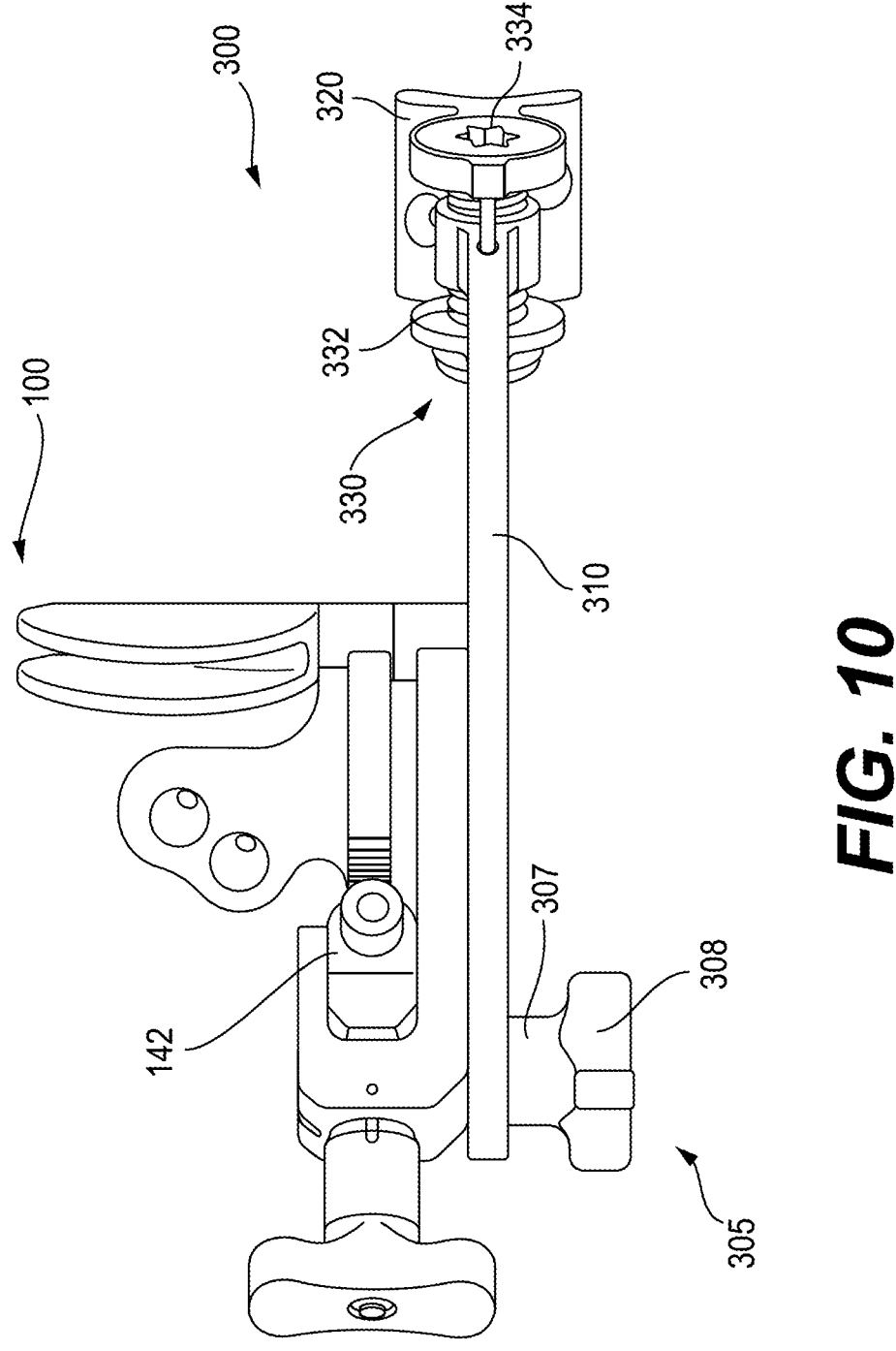
FIG. 10 is a diagram of a side view of the second reposition guide block and cutting guide of FIG. 8.

FIGS. 8 to 10 illustrate a second reposition guide block 300 applied to a cutting guide 100 according to an example embodiment of the present disclosure. In FIGS. 8 to 10, the first engagement structure 142 of the cutting guide 100 may be a worm gear/threaded component and the second engagement structure 132 of the cutting guide 100 may be a plurality of notches. In this case, the rotation arm 140 may include a separate indicator 146 (instead of having the first engagement structure 142 serve as an indicator). Most of the configurations/features/characteristics of the cutting guide 100 of FIGS. 8 to 10 may be similar to and/or same as the ones described above with respect to the cutting guide of FIGS. 1 to 2, and, thus, duplicate description may be omitted.

In some examples, the system may further include a second reposition guide block 300. The second reposition guide block 300 may be removably coupled to the cutting guide 100 (e.g., the rotation arm 140). The second reposition guide block may be provided to rotate the bone of the patient (e.g., first metatarsal bone). In some examples, the second reposition guide block 300 may rotate the bone of the patient (e.g., first metatarsal bone) in a third rotational direction 302. The third rotational direction 302 may be in the first (e.g., transverse) plane. In some examples, the third rotational direction 302 may be the same as the first rotational direction 121. In other examples, the third rotational direction 302 may be different from the first rotational direction 121.

The second reposition guide block 300 may include a second arm 310 removably coupled to the cutting guide 100 (e.g., the rotation arm 140). Although in FIGS. 8 to 10, the second reposition guide block 300 is coupled to the rotation arm 140 of the cutting guide 100, the second reposition guide block 300 can be coupled to any other suitable portion of the cutting guide 100. The second arm 310 may include a first end portion 312, a second end portion 314 opposite the first end portion 312, and a middle portion 316 between the first end portion 312 and the second end portion 314. In some examples, the cutting guide 100 may be positioned near the first end portion 312 or the middle portion 316 of the second arm 310.

In some examples, the second arm 310 may include a slot 318. The slot 318 may define a path/length along which the second reposition guide block 300 can translate/rotate relative to the cutting guide 100 (e.g., rotation arm 140). In some examples, the slot 318 may extend from the first end portion 312 to the middle portion 316 of the second arm 310. In other examples, the slot 318 may extend from the first end portion 312 to any other suitable portion of the second arm 310 (e.g., the second end portion 314) or only formed in the first end portion 312.

In some examples, a fastener 305 may be provided and inserted into the slot 318 to couple the second reposition guide block 300 (e.g., second arm 310) with the cutting guide 100 (e.g., rotation arm 140). In some examples, the cutting guide 100/rotation arm 140 may include a hole configured to receive the fastener. The fastener 305 may have a threaded engagement with the hole.

In some examples, the fastener 305 may include a first portion having a width smaller than the width of the slot 318 and a second portion 307 having a width larger than the width of the slot 318. Once the first portion is inserted into the slot 318 and ultimately into the hole of the cutting guide 100 (e.g., rotation arm 140), the second portion 307 may be pressed against the second arm 310, thereby temporarily fixing the second reposition guide block 300 (e.g., second arm 310) to the cutting guide 100.

In some examples, the fastener 305 may also include a graspable device 308 (e.g., knob). The graspable device 308 may be turned in one direction (e.g., clockwise direction) to fix the second reposition guide block 300 to the cutting guide 100. When the user wants to move the second reposition guide block 300 relative the cutting guide 100, for example, along the slot 318, the graspable device 308 may be turned in another direction (e.g., counter-clockwise direction). In this way, the second reposition guide block 300 can be locked/unlocked with the cutting guide 100. The second reposition guide block 300 can be fully disengaged from the cutting guide 100 when the graspable device 308 is fully turned in this direction and removed from the cutting guide 100.

In some examples, the second reposition guide block 300 may further include a second fixing block 320. The second fixing block 320 may be disposed at the second end portion 314 of the second arm 310. The second fixing block 320 may include a second fixing mechanism 322 for fixing the second fixing block 320 to the bone of the patient (e.g., first metatarsal bone). In some examples, the second fixing mechanism 322 may be one or more holes formed on the second fixing block 320. The one or more holes may be configured to receive a bone fastener. In other examples, the second fixing mechanism 322 may be a clamp or any other suitable device that can (temporally or removably) fix the second reposition guide block 300/second fixing block 320 to the bone of a patient (e.g., first metatarsal bone). The second fixing block 320 may be fixed to the bone of the patient percutaneously.

In some examples, the second fixing block 320 may include a base fixing block 321, a first protrusion 323, and a second protrusion 325. The first and second protrusions 323, 325 may extend from the base fixing block 321.

In some examples, the second reposition guide block 300 may further include a compressor 330. The compressor 330 may be disposed between the second arm 310 and the second fixing block 320. The compressor 330 may be configured to move the second fixing block 320 relative to the second arm 310 in a fourth direction 335 between a front position (e.g., toward the medial cuneiform bone) and a rear position (e.g., away from the medial cuneiform bone). In some examples, the fourth direction 335 may be in a third plane. The third plane may be a sagittal plane or substantially parallel to the sagittal plane (for example, when the second reposition guide block 300 is attached to the human body).

In some examples, the compressor 330 may include a threaded fastener 332. The second arm 310 may include a through hole configured to receive the compressor 330, for example, at the second end portion 314. The through hole of the second arm 310 may be in a threaded engagement with the compressor 330 (e.g., having a female thread). In this case, the rotation of the threaded fastener 332 may move the threaded fastener 332 relative to the second arm 310 between the front position and the rear position. In other examples, the compressor 330 may move back and forth in any other suitable manner (e.g., simply pushing or pulling the compressor 330 back and forth).

The compressor 330 may include a middle portion and end portions. The second arm 310 may be connected to the middle portion of the compressor 330 via the hole at the second end portion 314, and the second fixing block 320 may be connected to the end portions of the compressor 330 via the first and second protrusions 323, 325. The first and second protrusions 323, 325 may be permanently coupled to the compressor 330. Therefore, the second fixing block 320 may move together with the compressor 330 (when the compressor 330 is turned) in the fourth direction 335.

In some examples, the compressor 330 may include a driver-engagement recess 334. In this case, the compressor 330 can be turned/rotated through a driver that is configured to be engaged with the driver-engagement recess 334, thereby translating between the front position and the rear position.

Figure 11:
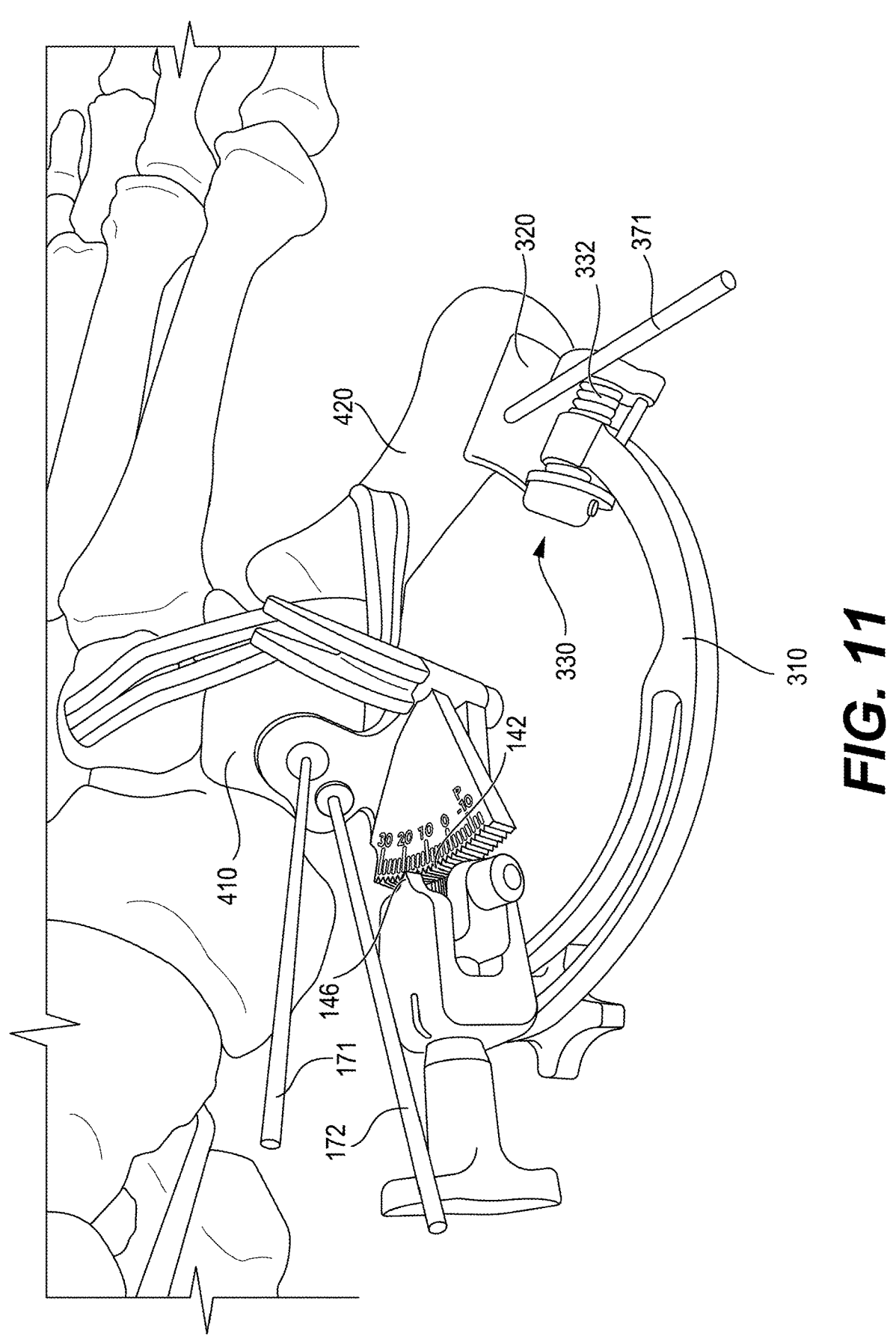
FIG. 11 is a diagram of the second reposition guide block and cutting guide of FIG. 8 applied to human bones.

FIG. 11 illustrates the second reposition guide block 300 and cutting guide 100 of FIGS. 8 to 10 applied to human bones. In FIG. 1, the skin of the foot is omitted for illustrative purposes only. As shown in FIG. 11, one or more bone fasteners 171/172 may pass the one or more holes 114 formed on/in the base body 110/first fixing block 112 and be inserted into the medial cuneiform bone, for example, to temporarily fix the base body 110/first fixing block 112 with the body (e.g., foot) of the patient. At this time, the cutting slot block 120 may be positioned adjacent the joint between the medial cuneiform bone and the first metatarsal bone.

In FIG. 11, the second reposition guide block 300 is coupled with the cutting guide 100 (e.g., rotation arm 140). As shown in FIG. 11, one or more bone fasteners 371 may pass the one or more holes formed on/in the second fixing block 320 and be inserted into the first metatarsal bone, for example, to temporarily fix the second reposition guide block 300/second fixing block 320 with the body (e.g., foot) of the patient.

In some examples, a first method for minimally invasive Lapidus surgery may be provided. The first method may include fixing the base body 110 of the cutting guide 100 to a first bone (e.g., medial cuneiform bone) of the patient. In some examples, the base body 110 may be fixed to the first bone of the patient by inserting a bone fastener, percutaneously, into the first bone through a hole 114 of the base body 110.

In some examples, the first method may further include positioning the cutting slot block 120 in a first angle (e.g., 0° or any other suitable angle). In some examples, the cutting slot block 120 may be temporarily fixed to the first angle by locking the position of the cutting slot block 120 via the rotation arm 140 (e.g., the graspable device 145). In some examples, the first angle may be marked as a reference point.

Then, one of the first bone (e.g., medial cuneiform bone) and a second bone (e.g., first metatarsal bone) may be cut (hereinafter "a first cut") by inserting, through the slot 127 of the cutting slot block 120 in the first angle, a bone cutting device (e.g., a bur) into an incision formed between the first bone and the second bone. In some examples, the cutting slot block 120 may be locked during the first cut at the first angle, and unlocked after the first cut.

Figure 12:
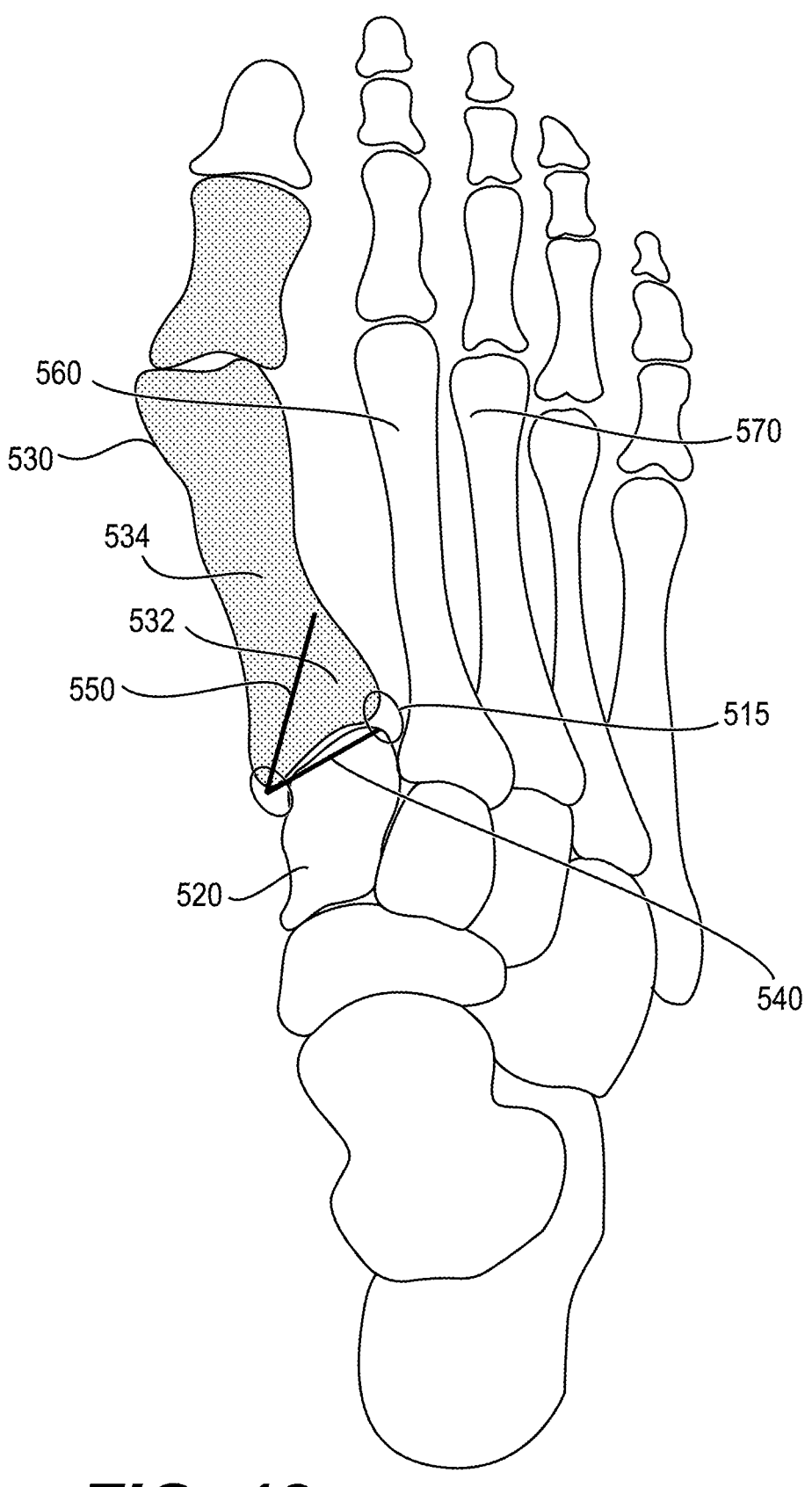
FIG. 12 is a diagram of a top view of an anatomical structure of a foot of a patient with bunion.

FIG. 12 is a diagram of a top view of an anatomical structure of a foot of a patient with a bunion. As shown in FIG. 12, a first incision 510 may be formed near a joint between the first bone 520 (e.g., medial cuneiform bone) and the second bone 530 (e.g., a first metatarsal bone), for example, on a side of the foot. In some examples, the first cut may be made along the line 540, for example, over the first bone 520 (e.g., medial cuneiform bone) and, in some cases, over the second bone 530 (in addition to the first bone 520). In some examples, the first cut line 540 may be substantially parallel to the joint line between the first bone 520 and the second bone 530. In some examples, the first cut may be intended to cut the surface on the first bone 520 (e.g., medial cuneiform bone) down to the bloody bone surface to prepare the first bone 520 for fusion.

Then, the cutting slot block 120 may be rotated to a second angle different from the first angle, and one of the first bone 520 and the second bone 530 may be cut (hereinafter "a second cut") by inserting, through the slot 127 of the cutting slot block 120 in the second angle, the bone cutting device into the incision. In some examples, the cutting slot block 120 may be temporarily fixed to the second angle by locking the position of the cutting slot block 120 via the rotation arm 140 (e.g., the graspable device 145). The slot 127 may be aligned with the rotation axis A1 of a hinge such that the angle of the cutting slot block 120 may be adjusted for the (first/second) cut through the same small incision 510.

In some examples, the size of the first incision 510 may be in a range of about 3 mm to about 10 mm, for example, about 3 mm to about 5 mm, about 5 mm to about 7 mm, about 7 mm to about 9 mm, and/or about 9 mm to about 10 mm. In other examples, the incision 510 may have any other suitable size (less than 3 mm or greater than 10 mm).

The difference between the second angle and the first angle may be in a range of about 10° to about 25°, for example, about 10° to about 15°, about 15° to about 20°, or about 20° to about 25°. In other examples, the difference between the second angle and the first angle may have any other suitable ranges (e.g., less than 10° or greater than 25°).

In some examples, the second cut may be made along the line 550 to cut the second bone 530. The first cut line 540 may include a first end near the incision 510 and a second end opposite the first end. The second cut line 550 may include a first end near the incision 510 and a second end opposite the first end. In some examples, the distance between the first end of the first cut line 540 and the first end of the second cut line 550 may be smaller than the distance between the second end of the first cut line 540 and the second end of the second cut line 550. In some examples, the first end of the first cut line 540 and the first end of the second cut line 550 may meet at the same point. That is, the first cut and the second cut may have the same (or almost the same) starting point. In some examples, the first end of the first cut line 540 and the first end of the second cut line 550 may be located within the slot 127 of the cutting guide 100 and/or on the rotation axis A1.

In some examples, the distance between the first end of the first cut line 540 and the first end of the second cut line 550 may be smaller than the size of the first incision 510 (or a half of it). For example, the distance between the first end of the first cut line 540 and the first end of the second cut line 550 may be smaller than 3 mm, smaller than 2 mm, smaller than 1.5 mm, smaller than 1 mm, smaller than 0.5 mm, smaller than 0.3 mm, or smaller than 0.1 mm.

A portion of the first bone 520 and/or the second bone 530 that is cut by the bone cutting device may be removed. For example, the bone 532 cut by the first and second cuts may be removed. In some examples, the portion of the first bone 520 and/or the second bone 530 that is cut by the bone cutting device may be in a wedge shape as shown in FIG. 12.

In some examples, when or before removing the cut bone 532, cartilage and any tissue that may prevent the fusion between the remaining first/second bone may be removed. In some examples, one or more additional incisions are provided. For example, a second incision 515 may be provided on the dorsal/top side of the foot. The surgeon may run irrigation through the second incision 515 to clear out debris and any removed materials. The size of the second incision 515 may be the same as or similar to the size of the first incision 510. The second incision 515 may be provided also to protect soft tissues that should not be cut/removed (e.g., blood vessels, tendons, muscles) during the first/second cuts. For example, a blocking device may be provided through the second incision 515 to prevent the bone cutting device (e.g., a bur) from cutting the soft tissues that need to be protected.

In some examples, after the cut bone (e.g., wedge 532) is removed, the distal end of the second bone 530 may be pulled back towards a third bone 560 (e.g., second metatarsal bone) so that the second bone 530 is aligned with other bones (e.g., other metatarsal bones). In this process and/or through a separate process, the remaining portion 534 of the second bone 530 may be pushed close to the first bone 520, and fused together (e.g., the first metatarsal screwed, plated, or affixed through any appropriate means such as pins, internal nails, or staples to the medial cuneiform) so that those two bones are brought together to form one new bone without a joint. Then, the (human) body may initiate a healing process, which may grow the two bones together.

In some examples, prior to fixing the base body 110 to the first bone of the patient, the cutting guide may be placed along the first bone 520, a bone fastener may be inserted into a joint between the first bone 520 and the second bone 530, and then the bone fastener may be positioned in the slot 127 of the cutting slot block 120 to ensure proper alignment of the cutting guide 100/cutting slot block 120 with the joint.

This may help the surgeon visualize the rest of the joint that the surgeon cannot see from the incision 510 and set/adjust the angle of the cutting slot block 120.

In some examples, the method may further include, prior to fixing the base body 110 to the first bone of the patient, fixing a first reposition guide block 200 to a third bone (e.g., second metatarsal bone 560 or a third metatarsal bone 570) of the patient using a first bone fastener by inserting the first bone fastener, percutaneously, into the third bone through a hole 220 in a second portion 204 of the first reposition guide block 200. The first reposition guide block 200 may be configured to provide a guide for rotating the second bone 530 (e.g., first metatarsal bone) of the patient in a second rotational direction 205.

Then, a second bone fastener may be inserted, percutaneously, into the second bone 530 through an elongated slot 210 in a first portion 202 of the first reposition guide block 200. The second bone 530 may be rotated in the second rotational direction 205 using the second bone fastener. For examples, the second bone 530 may be rotated along the elongated slot 210 around an axis of the second bone 530 using the second bone fastener, for example, in the second (e.g., frontal) plane. After the second plane correction of the second bone 530, a side of the second bone fastener may be placed into one of the grooves 213/125 on a first/second elongated surface 212/214 of the elongated slot 210 (or when the grooves 213/215 are sized smaller than the bone fastener, the elongated slot 210 may clamp the bone fastener from the sides) to prevent a rotation of the second bone 530 in the second rotational direction 205 in the second plane. This may prevent the second bone 530 from rotating back to its original position after the second plane correction of the second bone 530. The second plane correction may be completed before the first and second cuts.

In some examples, a second method for minimally invasive Lapidus surgery may be provided. The second method may include fixing the base body 110 of the cutting guide 100 to a first bone (e.g., medial cuneiform bone) of the patient. In some examples, the base body 110 may be fixed to the first bone of the patient by inserting a bone fastener, percutaneously, into the first bone through a hole 114 of the base body 110.

Figure 13:
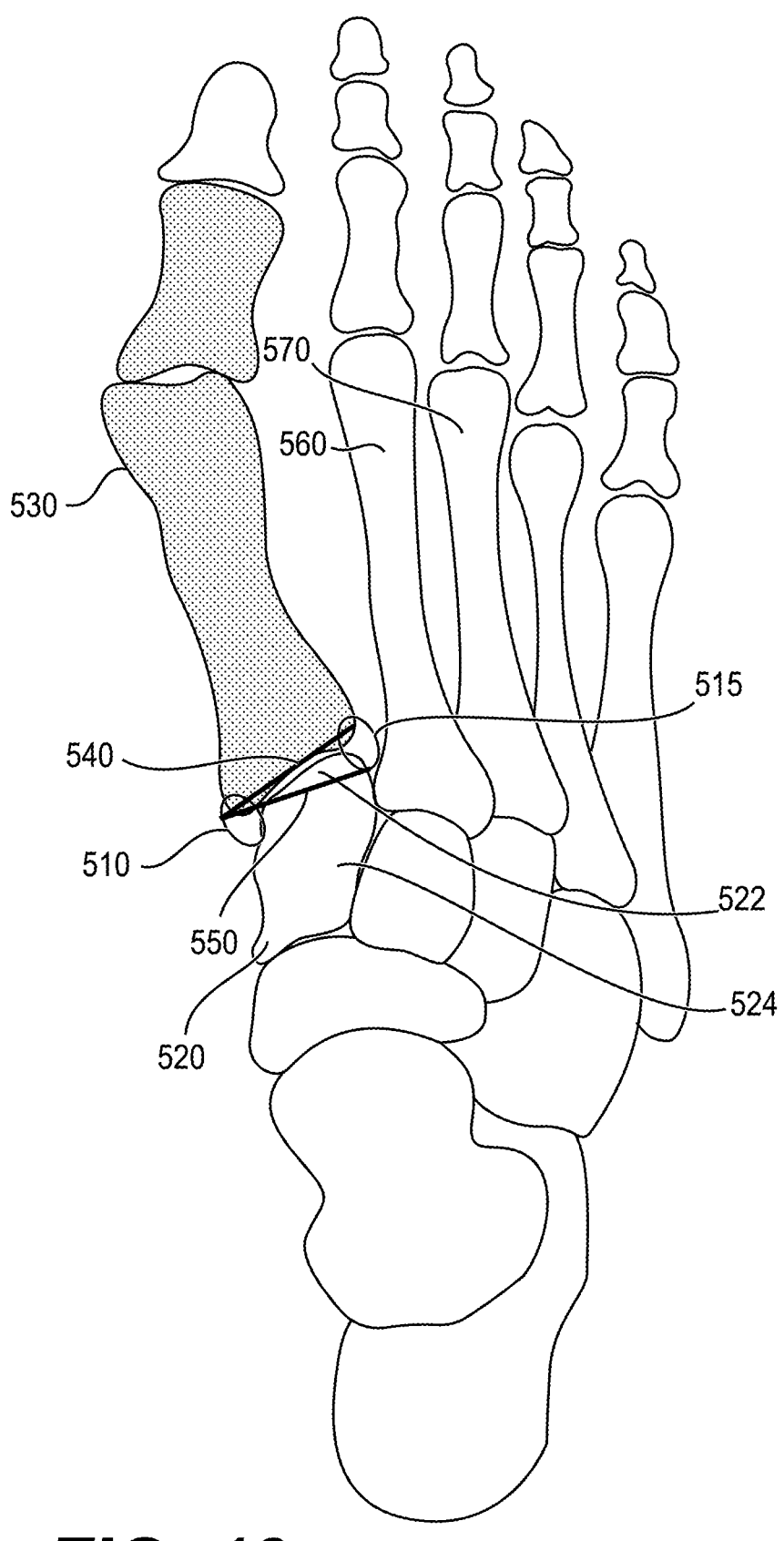
FIG. 13 is a diagram of a top view of an anatomical structure of a foot of a patient with bunion.

Referring to FIG. 13, in the second method, a first cut 540 may be made along the line 540, for example, over the second bone 530 (e.g., first metatarsal bone). In some examples, the first cut line 540 may be substantially parallel to the joint line between the first bone 520 and the second bone 530. In some examples, the first cut 540 may be intended to cut the surface on the second bone 530 (e.g., first metatarsal bone) down to the bloody bone surface to prepare the second bone 530 for fusion.

In the second method, a second cut 550 may be made along the line 550 to cut the first bone 520 (e.g., medial cuneiform bone). The first cut line 540 may include a first end near the incision 510 and a second end opposite the first end. The second cut line 550 may include a first end near the incision 510 and a second end opposite the first end. In some examples, the distance between the first end of the first cut line 540 and the first end of the second cut line 550 may be smaller than the distance between the second end of the first cut line 540 and the second end of the second cut line 550. In some examples, the first end of the first cut line 540 and the first end of the second cut line 550 may meet at the same point. That is, the first cut and the second cut may have the same (or almost the same) starting point. In some examples, the first end of the first cut line 540 and the first end of the second cut line 550 may be located within the slot 127 of the cutting guide 100 and/or on the rotation axis A1.

A portion of the first bone 520 and/or the second bone 530 that is cut by the bone cutting device may be removed. For example, the bone 522 cut by the second cut 550 may be removed.

In some examples, after the cut bone (e.g., bone 522) is removed, the second bone 530 may be pulled back towards a third bone 560 (e.g., second metatarsal bone) so that the second bone 530 is aligned with other bones (e.g., other metatarsal bones). In this process and/or through a separate process, the second bone 530 may be pushed close to the first bone 520, and fused together (e.g., the first metatarsal screwed, plated, or affixed through any appropriate means such as pins, internal nails, or staples to the medial cuneiform) so that those two bones are brought together to form one new bone without a joint.

Most of other/additional steps, processes, and/or features of the second method for minimally invasive Lapidus surgery may be similar to and/or same as the ones described above with respect to the first method (e.g., distance between the first end of the first cut line 540 and the first end of the second cut line 550, additional incisions, steps prior to fixing the base body 110), and, thus, duplicate description may be omitted.

If the first metatarsal bone is not corrected in the frontal plane, there could be a bone misalignment issue. For example, there are two little bones underneath the first metatarsal bone, called a sesamoid bone, and if the metatarsal bone is corrected only in the transverse plane, these bones may get out of the alignment, which may cause a significant unbalance in the soft tissue down around the toes. This may also cause various other bunion-associated problems. Aspects of the present disclosure may provide a way to correct the frontal plane rotation, for example, using the first reposition guide block 200 (and the third reposition guide block 600 as discussed in detail below), which may ensure that the sesamoid bones are back under the joint with the phalanges.

In some examples, prior to fixing the first reposition guide block 200 to the third bone, a soft tissue release may be performed, through the incision 510 on the medial side of the joint between the first bone 520 and the second bone 530, to free up the joint. The soft tissue to be released may include ligaments that may hold the first and second bones together. Some of this soft tissue may be cut or removed so that the second bone 530 can be moved around to correct the angle/position thereof. This soft tissue release may detach the second bone 530 from the first bone 520 and free up the space between these bones to prepare these two bones for fusion. The soft tissue release can be performed through a scalpel or any other suitable sharp device. After the soft tissue release, the connection between the first bone 520 and the second bone 530 may become loose, but to some extent it may still be held together though muscles and tendons. In some examples, a distraction device may be used to loosen the connection between the first and second bones.

In some examples, after the second bone 530 is repositioned and compressed against the first bone 520, and bone fasteners, such as k-wires, may be used for provisional fixation of the joint. For example, initially a tack/pin may be used to fix the cutting guide 100 to the first bone 520, and this may be replaced with a k-wire that may cross the joint for temporary fixation prior to removing the cutting guide 100. With the joint secure, the first reposition guide block 200 and other associated bone fasteners may be removed. The fixation of the first and second bones 520, 530 may be completed with cannulated screws placed over the k-wires used for provisional fixation, solid screws placed percutaneously, one or more small plates (e.g., smaller than the incision 510/515) inserted through the small incision 510/515, and/or any other suitable fixation method.

In some examples, the cutting guide 100 may be used with the second reposition guide block 300 to correct the alignment of the second bone 530. The second reposition guide block 300 may be used to move or rotate the second bone (e.g., first metatarsal bone) in the first (e.g., transverse) plane and/or in the third (e.g., sagittal) plane.

The second arm 310 of the second reposition guide block 300 may be removably coupled to the cutting guide 100 (e.g., the rotation arm 140), and the second fixing block 320 of the second reposition guide block 300 may be fixed to the second bone 530 of the patient percutaneously.

After the second cut, the cutting slot block 120/rotation arm 140 may be at the second angle. At this time, the second reposition guide block 300 may be locked with the translation arm 140/cutting guide 100. In this locked status, the translation arm 140/cutting guide 100 may be rotated, for example, to a third angle for the first (e.g., transverse) plane correction of the second bone. In some examples, the third angle may be the same as or similar to the first angle.

In some examples, the second bone 530 may be moved back and forth along the longitudinal axis of the second bone 530 by using the compressor 330 of the second reposition guide block 300. The second bone 530 coupled to the compressor 330 via the second fixing block 320 may be pushed towards the first bone 520 by pushing the compressor 330 in the forward direction for the third (sagittal) plane correction.

Figure 14:
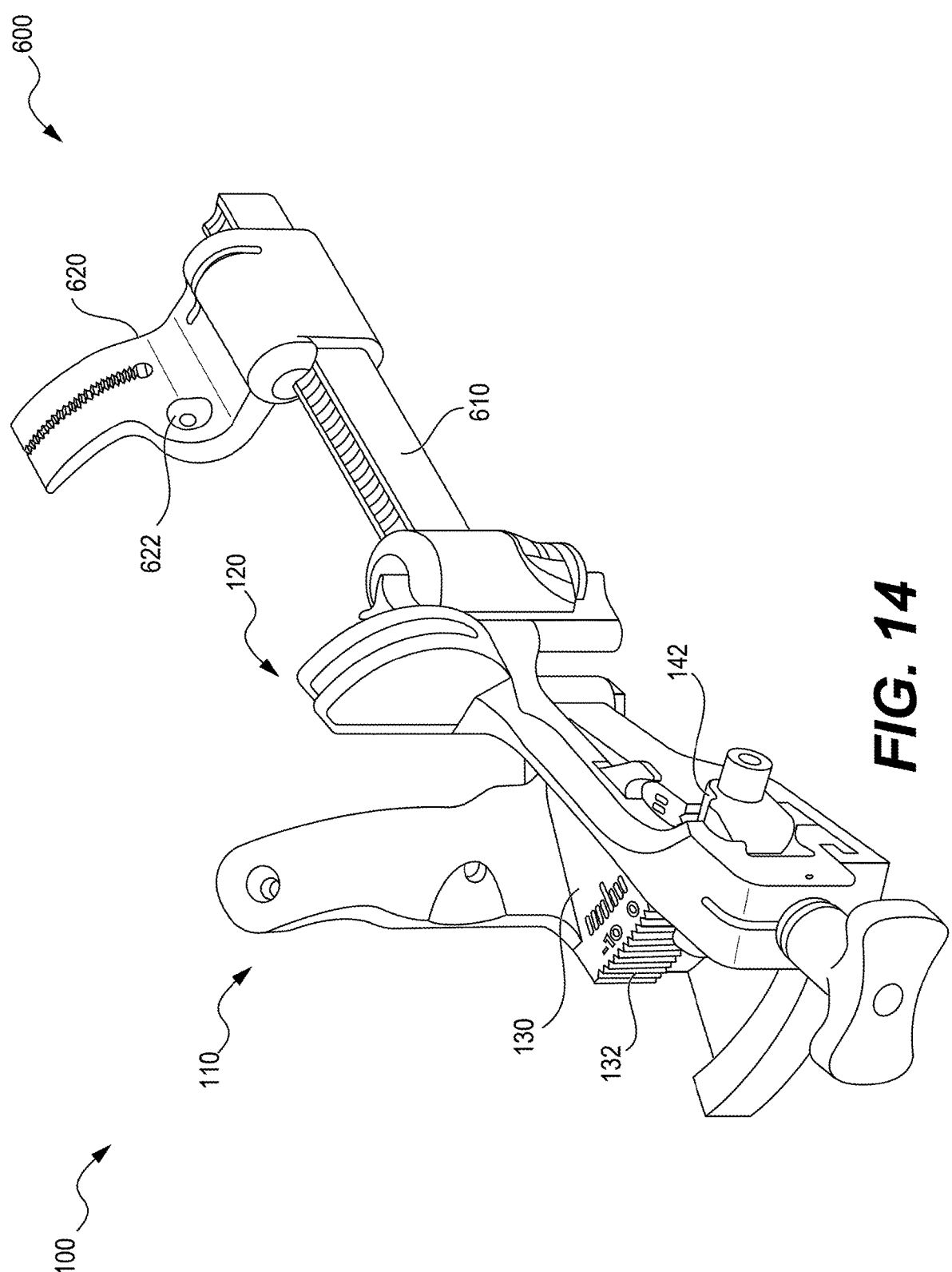
FIG. 14 is a diagram of a front left perspective view of a third reposition guide block applied to a cutting guide according to an example embodiment of the present disclosure.
Figure 15:
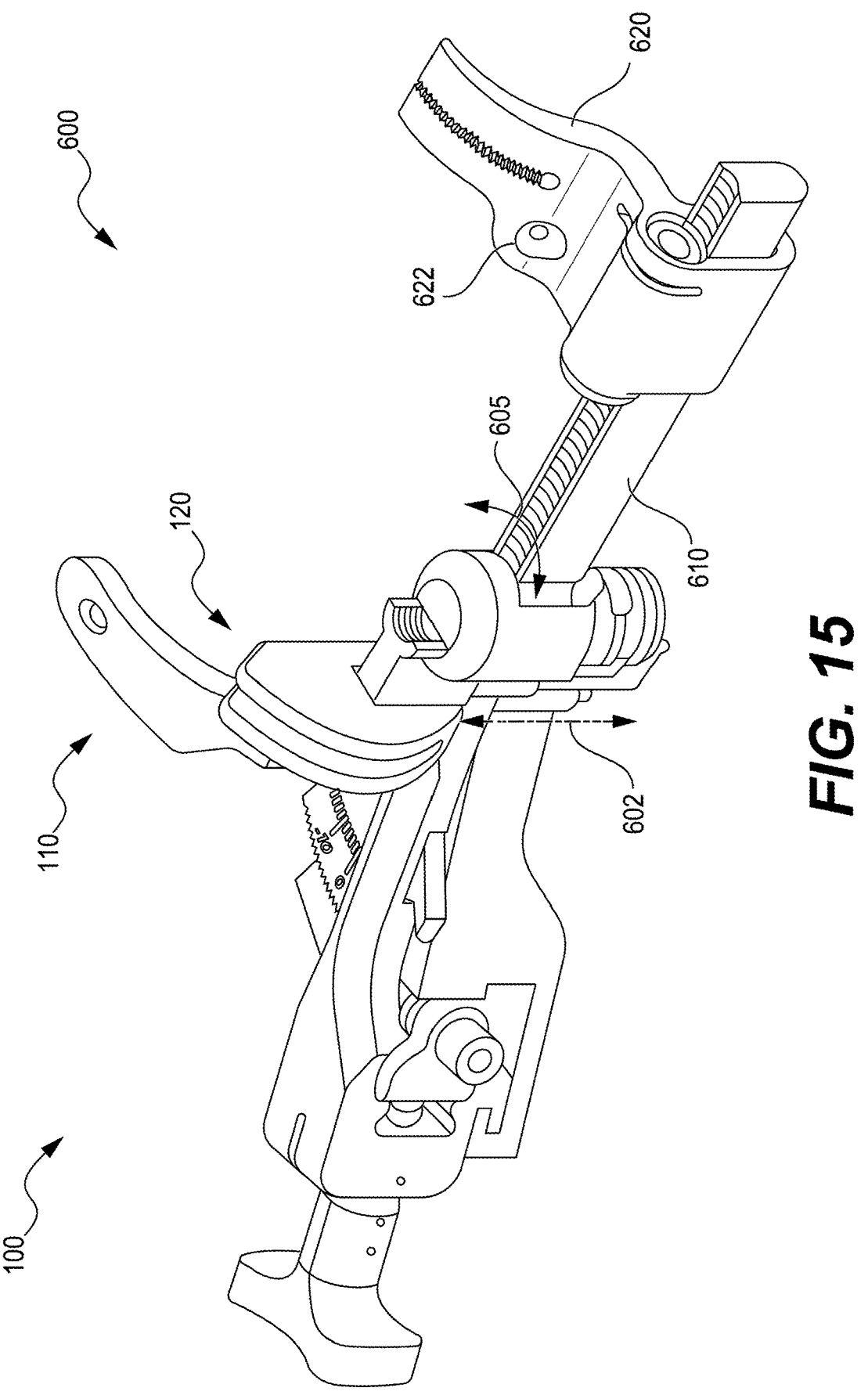
FIG. 15 is a diagram of a front right perspective view of the third reposition guide block and cutting guide of FIG. 14.

FIGS. 14 to 15 illustrate a third reposition guide block 600 applied to a cutting guide 100 according to an example embodiment of the present disclosure. The third reposition guide block 600 may be a combination of the first and second reposition guide blocks 200, 300 and/or may be able to provide a function provided by the first and second reposition guide blocks 200, 300. In FIGS. 14 to 15, the first engagement structure 142 of the cutting guide 100 may be a worm gear/threaded component and the second engagement structure 132 of the cutting guide 100 may be a plurality of notches. Most of the configurations/features/characteristics of the cutting guide 100 of FIGS. 14 to 15 may be similar to and/or same as the ones described above with respect to the cutting guide of FIGS. 1, 2, 8-10 and, thus, duplicate description may be omitted.

As shown in FIGS. 14 to 15, in some examples, the third reposition guide block 600 may mount to the cutting slot block 120 of the cutting guide 100. For example, one of the third reposition guide block 600 and the cutting slot block 120 may have a channel and the other may have a segment that fits within the channel. The third reposition guide block 600 may translate relative to the cutting slot block 120 (e.g. dorsal/plantar translation 602 and/or fourth rotational direction 605 in a transverse plane). In some examples, the third reposition guide block 600 may be translated by a threaded mechanism.

Figures 16, 17:
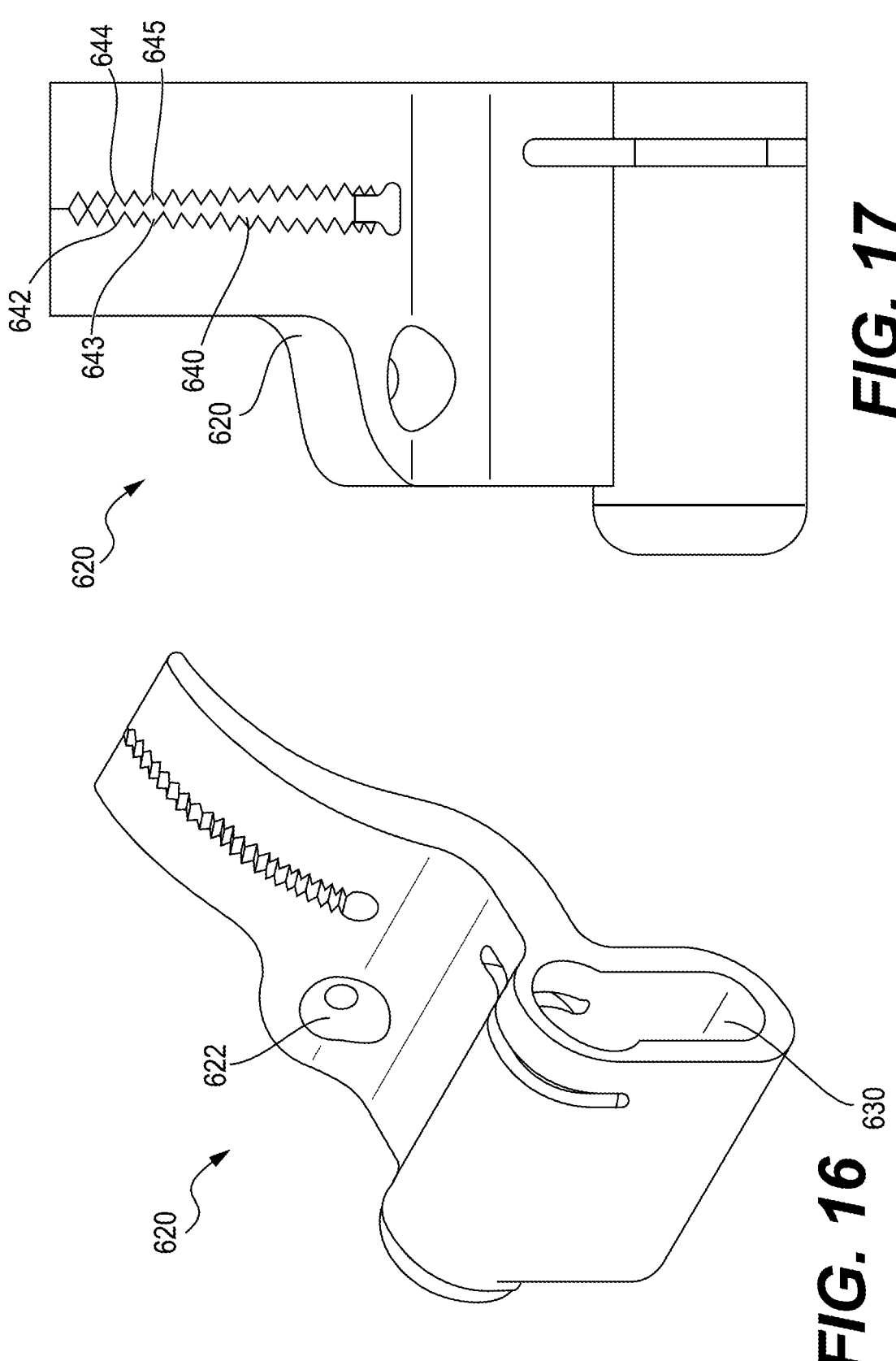
FIG. 16 is a diagram of a perspective view of a third fixing block of the third reposition guide block of FIG. 14.
FIG. 17 is a diagram of a side view of a third fixing block of the third reposition guide block of FIG. 14.

In some examples, the third reposition guide block 600 may include a third arm 610 and a third fixing block 620. The third arm 610 may extend away from the cutting slot block 120. Referring to FIG. 16, the third fixing block 620 may include a through hole or channel 630 configured to receive the third arm 610. The third fixing block 620 may move along the third arm 610 between a front position and a rear position. For example, the third fixing block 620 may include a threaded component retained in such a way to be in a threaded engagement with the third arm 610. In this case, the rotation of the threaded component may move the third fixing block 620 relative to the third arm 610 between the front position and the rear position.

In some examples, the third fixing block 620 may include a third fixing mechanism 622 for fixing the third fixing block 620 to the bone of the patient (e.g., first metatarsal bone). In some examples, the third fixing mechanism 622 may be one or more holes formed on the third fixing block 620. The one or more holes may be configured to receive a bone fastener. In other examples, the third fixing mechanism 622 may be a clamp or any other suitable device that can (temporally or removably) fix the third reposition guide block 600/third fixing block 620 to the bone of a patient (e.g., first metatarsal bone). The third fixing block 620 may be fixed to the bone of the patient percutaneously.

As shown in FIGS. 14 to 17, in some examples, the third fixing block 620 may include an elongated slot 640, provided to receive a bone fastener. In some examples, the elongated slot 640 may be the same as or similar to the elongated slot 210 of the first reposition guide block. In some examples, the elongated slot 640 may be tapered with an opening larger than the bone fastener at one end and a gap between opposing surfaces that becomes smaller than the bone fastener at the other end of the slot. The bone fastener may be inserted into the elongated slot 640 (and ultimately into the bone of the patient percutaneously) at the wide end of the slot and can be moved along the elongated slot 640 in the second rotational direction 205. The elongated slot 640 may include a first elongated surface 642 and a second elongated surface 644 opposite the first elongated surface 642. The first elongated surface 642 and/or the second elongated surface 644 may include a plurality of grooves 643/645 configured to receive the bone fastener. The surfaces of the elongated slot may press in on the bone fastener such that the grooves 643/645 prevent de-rotation of the bone fastener in the second rotational direction 205. Once the bone is rotated to the desired position along the second rotational direction 205, another bone fastener may be placed percutaneously through another hole in the third reposition guide block 600 to fix the rotation of the bone relative to the third reposition guide block 600 in this second rotational direction 205.

In some examples, the third arm 610 may define a first longitudinal axis and the elongated slot 640 may define a second longitudinal axis. The second longitudinal axis of the elongated slot 640 may be perpendicular to the first longitudinal axis of the third arm 610. Using the elongated slot 640 of the third reposition guide block 600, the user can correct the frontal plane rotation, which may ensure that the sesamoid bones are back under the joint with the phalanges.

Aspects of the present disclosure may guide a surgeon in making (wedge) osteotomies using a bone cutting device (e.g., bur) through a small incision for a minimally invasive surgery (MIS), particularly for a multi-planar Lapidus procedure. The cutting guide 100 according to the present disclosure allows the surgeon to make two cuts that may have almost the same starting point, which may enable the minimally invasive surgery with a smaller incision (e.g., around 3 mm) than the traditional approaches (e.g., having an approximately 3 cm incision), thereby having less scarring, shorter soft tissue healing times, and lower risk of infection compared to the traditional full exposure techniques.

Compared to other minimally invasive techniques in the related art, aspects of the present disclosure may allow for a greater degree of angular correction by allowing for a wedge osteotomy instead of a single-plane osteotomy. Furthermore, this approach to the wedge osteotomy may allow the surgeon to select the angle of the wedge cut intraoperatively, for example, based on the anatomy and allow for intermetatarsal angle corrections of more than 20°. In some examples, aspects of the present disclosure can be used for any closing (wedge) osteotomy (e.g., metatarsals, metacarpals, phalanges, tibia, radius, humerus).

EMBODIMENTS

Various aspects of the subject matter described herein are set out in the following numbered embodiments:

Embodiment 1. A system comprises a cutting guide comprising: a base body configured to be fixed to a first bone of a patient; and a cutting slot block configured to provide a guide for cutting at least one of the first bone and a second bone of the patient, wherein the cutting slot block is rotationally coupled to the base body, wherein the cutting slot block is configured to rotate in a first rotational direction, wherein the cutting guide comprises a distal portion and a proximal portion.

Embodiment 2. The system of embodiment 1, wherein the first bone comprises a medial cuneiform bone.

Embodiment 3. The system of embodiments 1-2, wherein the second bone comprise a first metatarsal bone.

Embodiment 4. The system of embodiments 1-3, wherein the cutting guide further comprises a gauge block configured to indicate an angle of the cutting slot block.

Embodiment 5. The system of embodiment 4, wherein a difference between a maximum and a minimum of the angle of the cutting slot block is at least 15°.

Embodiment 6. The system of embodiments 1-5, wherein the base body comprises a first fixing block, wherein the first fixing block includes a first fixing mechanism for fixing the base body to the first bone of the patient.

Embodiment 7. The system of embodiment 6, wherein the first fixing mechanism comprises at least one of a clamp and a hole configured to receive a bone fastener.

Embodiment 8. The system of embodiments 1-7, wherein the cutting slot block comprises: a cutting slot guide body; and a slot formed in or on the cutting slot guide body.

Embodiment 9. The system of embodiments 1-8, the cutting guide further comprises a rotation arm coupled to the cutting slot block and configured to rotate the cutting slot block relative to the base body, wherein the rotation arm extends outward from an axis of rotation of the cutting slot block.

Embodiment 10. The system of embodiment 9, wherein the rotation arm comprises a first engagement structure configured to engage and disengage the rotation arm with and from the base body.

Embodiment 11. The system of embodiment 10, wherein the base body comprises a second engagement structure, the second engagement structure configured to be engaged with the first engagement structure.

Embodiment 12. The system of embodiment 11, wherein the first engagement structure comprises a blade and the second engagement structure comprises notches.

Embodiment 13. The system of embodiments 10-12, wherein the rotation arm comprises a locking mechanism configured to lock an angle of the cutting slot block relative to the base body.

Embodiment 14. The system of embodiments 1-13, further comprising a first reposition guide block configured to provide a guide for rotating the second bone of the patient in a second rotational direction.

Embodiment 15. The system of embodiment 14, wherein the first reposition guide block comprises a first portion having an elongated slot.

Embodiment 16. The system of embodiment 15, wherein the first portion is curved.

Embodiment 17. The system of embodiments 15-16, wherein the elongated slot includes a first elongated surface and a second elongated surface opposite the first elongated surface, wherein at least one of the first elongated surface and the second elongated surface comprises a plurality of grooves.

Embodiment 18. The system of embodiments 14-17, wherein the first reposition guide block comprises a second portion having one or more holes configured to receive a bone fastener.

Embodiment 19. The system of embodiments 1-18, further comprising a second reposition guide block removably coupled to the rotation arm, wherein the second reposition guide block is configured to rotate the second bone of the patient.

Embodiment 20. The system of embodiment 19, wherein the second reposition guide block is configured to rotate the second bone of the patient in the first rotational direction.

Embodiment 21. The system of embodiments 19-20, wherein the second reposition guide block comprises: a second arm removably coupled to the rotation arm, wherein the second arm comprises a first end portion at the cutting guide and a second end portion opposite the first end portion; and a second fixing block disposed at the second end portion, wherein the second fixing block includes a second fixing mechanism for fixing the second fixing block to the second bone of the patient.

Embodiment 22. The system of embodiment 21, wherein the second fixing mechanism comprises at least one of a clamp and a hole configured to receive a bone fastener.

Embodiment 23. The system of embodiments 21-22, wherein the second reposition guide block further comprises a compressor configured to move the second fixing block relative to the second arm between a front position and a rear position.

Embodiment 24. The system of embodiment 23, wherein the compressor comprises a threaded fastener.

Embodiment 25. The system of embodiments 23-24, wherein the compressor comprises a driver-engagement recess.

Embodiment 26. The system of embodiments 23-25, wherein the compressor is disposed between the second arm and the second fixing block.

Embodiment 27. The system of embodiments 19-26, wherein the second reposition guide block is configured to move relative to the rotation arm.

Embodiment 28. The system of embodiments 1-27, wherein the cutting slot block is disposed at the distal portion of the cutting guide.

Embodiment 29. A method of using the system of embodiments 1-28 comprises: fixing the base body of the cutting guide to the first bone of the patient; positioning the cutting slot block in a first angle; cutting at least one of the first bone and the second bone by inserting, through a slot of the cutting slot block in the first angle, a bone cutting device into an incision between the first bone and the second bone; rotating the cutting slot block to a second angle different from the first angle; and cutting at least one of the first bone and the second bone by inserting, through the slot of the cutting slot block in the second angle, the bone cutting device into the incision.

Embodiment 30. The method of embodiment 29, further comprising removing a portion of the first bone and/or the second bone that is cut by the bone cutting device.

Embodiment 31. The method of embodiment 30, wherein the portion of the first bone or the second bone that is cut by the bone cutting device is in a wedge shape.

Embodiment 32. The method of embodiments 29-31, wherein a size of the incision is in a range of about 3 mm to about 10 mm.

Embodiment 33. The method of embodiments 29-32, further comprising locking the cutting slot block in the first angle.

Embodiment 34. The method of embodiments 29-33, wherein the base body is fixed to the first bone of the patient by inserting a bone fastener, percutaneously, into the first bone through a hole of the base body.

Embodiment 35. The method of embodiments 29-34, further comprising, prior to fixing the base body to the first bone of the patient, placing the cutting guide along the first bone; inserting a bone fastener or other thin, straight device into a joint between the first bone and the second bone; and positioning the bone fastener in a slot of the cutting slot block to ensure proper alignment with the joint.

Embodiment 36. The method of embodiments 29-35, further comprising, prior to fixing the base body to the first bone of the patient, fixing a first reposition guide block to a third bone of the patient using a first bone fastener by inserting the first bone fastener, percutaneously, into the third bone through a hole in a second portion of the first reposition guide block, wherein the first reposition guide block is configured to provide a guide for rotating the second bone of the patient in a second rotational direction; inserting a second bone fastener, percutaneously, into the second bone through an elongated slot in a first portion of the first reposition guide block; and rotating the second bone in the second rotational direction using the second bone fastener; and placing a side of the second bone fastener into or around one of the grooves on a first or second elongated surface of the elongated slot to prevent a rotation of the second bone in the second rotational direction.

Embodiment 37. The method of embodiment 36, wherein the third bone comprises at least one of a second metatarsal bone and a third metatarsal bone.

As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

Reference throughout the specification to "various aspects," "some aspects," "some examples," "other examples," "some cases," or "one aspect" means that a particular feature, structure, or characteristic described in connection with the aspect is included in at least one example. Thus, appearances of the phrases "in various aspects," "in some aspects," "certain embodiments," "some examples," "other examples," "certain other embodiments," "some cases," or "in one aspect" in places throughout the specification are not necessarily all referring to the same aspect. Furthermore, the particular features, structures, or characteristics illustrated or described in connection with one example may be combined, in whole or in part, with features, structures, or characteristics of one or more other aspects without limitation.

When the position relation between two parts is described using the terms such as "on," "above," "below," "under," and "next," one or more parts may be positioned between the two parts unless the terms are used with the term "immediately" or "directly." Similarly, as used herein, the terms "coupled," "attachable," "attached," "connectable," "connected," or any similar terms may include directly or indirectly coupled, directly or indirectly attachable, directly or indirectly attached, directly or indirectly connectable, and directly or indirectly connected.

It is to be understood that at least some of the figures and descriptions herein have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein.

The terminology used herein is intended to describe particular embodiments only and is not intended to be limiting of the present disclosure. As used herein, the singular forms "a," "an," and "the" are intended to include the plural forms as well, unless otherwise indicated. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "at least one of X or Y" or "at least one of X and Y" should be interpreted as X, or Y, or X and Y.

It should be understood that various changes and modifications to the examples described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A system comprising:
a cutting guide comprising:
  a base body configured to be fixed to a first bone of a patient;
  a cutting slot block configured to provide a guide for cutting at least one of the first bone and a second bone of the patient, the cutting slot block rotationally coupled to the base body, and the cutting slot block configured to rotate in a first rotational direction; and
  a rotation arm coupled to the cutting slot block and configured to rotate the cutting slot block relative to the base body, the rotation arm extending outward from an axis of rotation of the cutting slot block, and the rotation arm comprising:
    a blade configured to engage and disengage the rotation arm with and from the base body, and
    a plurality of notches configured to be engaged with the blade,
  wherein the cutting guide comprises a distal portion and a proximal portion.

2. The system of claim 1, wherein the first bone comprises a medial cuneiform bone, and wherein the second bone comprise a first metatarsal bone.

3. The system of claim 1, wherein the cutting guide further comprises a gauge block configured to indicate an angle of the cutting slot block.

4. The system of claim 3, wherein a difference between a maximum and a minimum of the angle of the cutting slot block is at least 15°.

5. The system of claim 3, wherein the base body comprises a first fixing block, wherein the first fixing block includes a first fixing mechanism for fixing the base body to the first bone of the patient.

6. The system of claim 5, wherein the first fixing mechanism comprises at least one of a clamp and a hole configured to receive a bone fastener.

7. The system of claim 1, wherein the cutting slot block comprises:

a cutting slot guide body; and a slot formed in or on the cutting slot guide body.

8. The system of claim 1, wherein the rotation arm comprises a locking mechanism configured to lock an angle of the cutting slot block relative to the base body.

9. The system of claim 1, further comprising a reposition guide block removably coupled to the rotation arm, wherein the reposition guide block is configured to rotate the second bone of the patient.

10. The system of claim 9, wherein the reposition guide block is configured to rotate the second bone of the patient in the first rotational direction.

11. The system of claim 9, wherein the reposition guide block comprises:

a second arm removably coupled to the rotation arm, wherein the second arm comprises a first end portion at the cutting guide and a second end portion opposite the first end portion; and a second fixing block disposed at the second end portion, wherein the second fixing block includes a second fixing mechanism for fixing the second fixing block to the second bone of the patient.

12. The system of claim 11, wherein the second fixing mechanism comprises at least one of a clamp and a hole configured to receive a bone fastener.

13. The system of claim 11, wherein the reposition guide block further comprises a compressor configured to move the second fixing block relative to the second arm between a front position and a rear position.

14. The system of claim 13, wherein the compressor comprises a threaded fastener and/or a driver-engagement recess.

15. The system of claim 13, wherein the compressor is disposed between the second arm and the second fixing block.

16. The system of claim 9, wherein the reposition guide block is configured to move relative to the rotation arm.

17. The system of claim 1, wherein the cutting slot block is disposed at the distal portion of the cutting guide.

18. A system comprising:

a cutting guide comprising:

a base body configured to be fixed to a first bone of a patient; and a cutting slot block configured to provide a guide for cutting at least one of the first bone and a second bone of the patient, the cutting slot block rotationally coupled to the base body, and the cutting slot block configured to rotate in a first rotational direction, wherein the cutting guide comprises a distal portion and a proximal portion; and a reposition guide block removably coupled to a rotation arm of the cutting guide, the reposition guide block configured to rotate the second bone of the patient, and the reposition guide block comprising:

a second arm removably coupled to the rotation arm, the second arm comprising a first end portion at the cutting guide and a second end portion opposite the first end portion, a second fixing block disposed at the second end portion, the second fixing block including a second fixing mechanism for fixing the second fixing block to the second bone of the patient, and a compressor configured to move the second fixing block relative to the second arm between a front position and a rear position.

19. The system of claim 18, wherein the first bone comprises a medial cuneiform bone, and wherein the second bone comprise a first metatarsal bone.

20. The system of claim 18, wherein the cutting guide further comprises a gauge block configured to indicate an angle of the cutting slot block.

21. The system of claim 20, wherein a difference between a maximum and a minimum of the angle of the cutting slot block is at least 15°.

22. The system of claim 20, wherein the base body comprises a first fixing block, wherein the first fixing block includes a first fixing mechanism for fixing the base body to the first bone of the patient.

23. The system of claim 22, wherein the first fixing mechanism comprises at least one of a clamp and a hole configured to receive a bone fastener.

24. The system of claim 18, wherein the cutting slot block comprises:

a cutting slot guide body; and a slot formed in or on the cutting slot guide body.

25. The system of claim 18, wherein the rotation arm is coupled to the cutting slot block and configured to rotate the cutting slot block relative to the base body, wherein the rotation arm extends outward from an axis of rotation of the cutting slot block.

26. The system of claim 25, wherein the rotation arm comprises:

a first engagement structure configured to engage and disengage the rotation arm with and from the base body; and a second engagement structure, the second engagement structure configured to be engaged with the first engagement structure.

27. The system of claim 26, wherein the rotation arm comprises a locking mechanism configured to lock an angle of the cutting slot block relative to the base body.

28. The system of claim 18, wherein the second fixing mechanism comprises at least one of a clamp and a hole configured to receive a bone fastener.

29. The system of claim 18, wherein the compressor comprises a threaded fastener and/or a driver-engagement recess.

30. The system of claim 18, wherein the compressor is disposed between the second arm and the second fixing block.

31. The system of claim 18, wherein the reposition guide block is configured to move relative to the rotation arm.

32. The system of claim 18, wherein the cutting slot block is disposed at the distal portion of the cutting guide.

\* \* \* \* \*